(12) United States Patent
Ryan et al.

(10) Patent No.: US 9,493,566 B2
(45) Date of Patent: Nov. 15, 2016

(54) ANTIBODIES TO INTEGRIN AVB6 AND USE OF SAME TO TREAT CANCER

(71) Applicant: Seattle Genetics, Inc., Bothell, WA (US)

(72) Inventors: Maureen Ryan, Bellevue, WA (US); Sussman Django, Seattle, WA (US)

(73) Assignee: Seattle Genetics, Inc., Bothell, WA (US)

( * ) Notice: Subject to any disclaimer, the term of this patent is extended or adjusted under 35 U.S.C. 154(b) by 131 days.

(21) Appl. No.: 14/378,746

(22) PCT Filed: Feb. 14, 2013

(86) PCT No.: PCT/US2013/026087
§ 371 (c)(1),
(2) Date: Aug. 14, 2014

(87) PCT Pub. No.: WO2013/123152
PCT Pub. Date: Aug. 22, 2013

(65) Prior Publication Data
US 2016/0009806 A1 Jan. 14, 2016

Related U.S. Application Data

(60) Provisional application No. 61/602,511, filed on Feb. 23, 2012, provisional application No. 61/600,499, filed on Feb. 17, 2012.

(51) Int. Cl.
| | | |
|---|---|---|
| *C07K 16/00* | (2006.01) | |
| *C07K 16/28* | (2006.01) | |
| *C07K 16/46* | (2006.01) | |
| *A61K 39/395* | (2006.01) | |
| *C07H 21/04* | (2006.01) | |
| *A61K 47/48* | (2006.01) | |
| *C07K 19/00* | (2006.01) | |
| *A61K 39/00* | (2006.01) | |

(52) U.S. Cl.
CPC ..... *C07K 16/2839* (2013.01); *A61K 47/48384* (2013.01); *A61K 47/48561* (2013.01); *C07K 19/00* (2013.01); *A61K 2039/505* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | |
|---|---|---|
| 5,962,643 A | 10/1999 | Sheppard et al. |
| 7,150,871 B2 | 12/2006 | Huang et al. |
| 7,465,449 B2 | 12/2008 | Violette |
| 7,943,742 B2 | 5/2011 | Violette et al. |
| 8,398,975 B2 | 3/2013 | Rinkenberger et al. |
| 8,491,901 B2 | 7/2013 | Imai et al. |
| 2004/0048312 A1 | 3/2004 | Li et al. |
| 2005/0090648 A1 | 4/2005 | Tsurushita et al. |
| 2005/0287538 A1 | 12/2005 | Cheung et al. |
| 2006/0204506 A1 | 9/2006 | Ebel et al. |
| 2009/0028853 A1 | 1/2009 | Sheppard et al. |
| 2011/0059469 A1 | 3/2011 | Aburatani et al. |
| 2011/0046309 A1 | 4/2011 | Cho et al. |
| 2011/0294982 A1 | 12/2011 | Vanlandschoot et al. |

FOREIGN PATENT DOCUMENTS

| | | |
|---|---|---|
| WO | 2006041934 | 4/2006 |
| WO | 2007026000 | 3/2007 |
| WO | 2011/046309 | 4/2011 |
| WO | 2013148316 | 10/2013 |

OTHER PUBLICATIONS

Ryan et al. Integrin αVβ6 is expressed on multiple solid tumors and is a potential therapeutic target for auristatin-based antibody-drug conjugates. AACR; Cancer Res 2012;72(8 Suppl):Abstract nr 4630. doi:1538-7445.AM2012-4630.*
Munk, C. et al., Uniprot Submission with Accession No. D3Q6V1 [online] Nov. 30, 2010.
Tanfous, N.G.B. et al., Characterization of a Novel Monoclonal Antibody with Restricted Specificity to the Free b2 Integrin aM CD11b Subunit. Hybridoma, vol. 26(6), pp. 373-379: Table 2 abstract, 2007.
Ryan et al., Integrin alphaValpha6 is expressed on multiple solid tumors and is a potential therapeutic target for auristatin-based antibody-drug conjugates, Cancer Research, vol. 72, issue 8, suppl 1, abstract 4630, 2012.
Ryan, et al., Integrin AVB6 is Expressed on Multiple Solid Tumors and is a Potential Therapeutic Target for Auristatin-Based Antibody-Drug Conjugates poster, Abstract No. 4630, American Association of Cancer Research, Apr. 1-4, 2012, Chicago, IL.

* cited by examiner

*Primary Examiner* — Maher Haddad
(74) *Attorney, Agent, or Firm* — Seattle Genetics, Inc.

(57) ABSTRACT

The invention provides antibodies that specifically bind to integrin αvβ6. The antibodies are useful for treatment and diagnoses of various cancers as well as detecting αvβ6.

13 Claims, 14 Drawing Sheets

```
                       10        20        30        40        50
                ....|....|....|....|....|....|....|....|....|....|....|....
SEQ ID NO: 1
m15H3  vH       E...Q...P.LV.......I.......S.S.......K.SH..S...I............
SEQ ID NO: 9
h15H3  HA       QVQLVQSGAEVKKPGASVKVSCKASGYTFTGYFMNWVRQAPGQGLEWMGLINPYNGDSFY
SEQ ID NO: 11
h15H3  HB       ............................S.S............................
SEQ ID NO: 15
h15H3  HL       ............................S.S............................
SEQ ID NO: 17
h15H3  HN       ............................S.S............................
SEQ ID NO: 22
h15H3  HT       ............................S.S............................
SEQ ID NO: 23
h15H3  HU       ............................S.S............................

70        80        90       100       110
                |....|....|....|....|........|....|....|....|....|....|...
m15H3  vH       ......KA.L.VQK.S..AH...Q..T...S..F..V..............PL....
h15H3  HA       NQKFKGRVTMTRDTSTSTVYMELSSLRSEDTAVYYCARGLRRDFDYWGQGTLVTVSS
h15H3  HB       .........................................................
h15H3  HL       ............K.S..A.......................................
h15H3  HN       ............Q............................................
h15H3  HT       ............Q............................V..............
h15H3  HU       ............QK.S..A......................V..............

10        20        30        40        50
                ....|....|....|....|....|....|........|....|....|....|....|
SEQ ID NO: 2
m15H3  vL       ...L..I..T.S..I.....LF................LF......K..........
SEQ ID NO: 10
h15H3  LA       DVVMTQSPLSLPVTLGQPASISCKSSQSLLDSDGKTYLNWFQQRPGQSPRRLIYLVSELD
SEQ ID NO: 25
h15H3  LC       ......................................LF...................
SEQ ID NO: 28
h15H3  LF       ....................LF................LF.......K...........
SEQ ID NO: 29
h15H3  LG       ...L..................................LF...................

60        70        80        90       100
                ....|....|....|....|....|....|....|....|....|....|....|...
m15H3  vL       .......T................L................................
h15H3  LA       SGVPDRFSGSGSGTDFTLKISRVEAEDVGVYYCWQGTHFPRTFGGGTKLEIKR
h15H3  LC       .....................................................
h15H3  LF       .......T.............................................
h15H3  LG       .....................................................
```

Figure 1

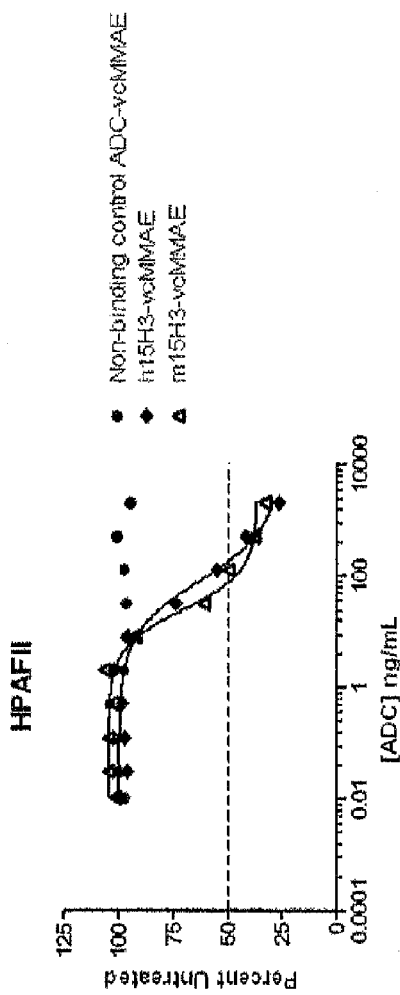
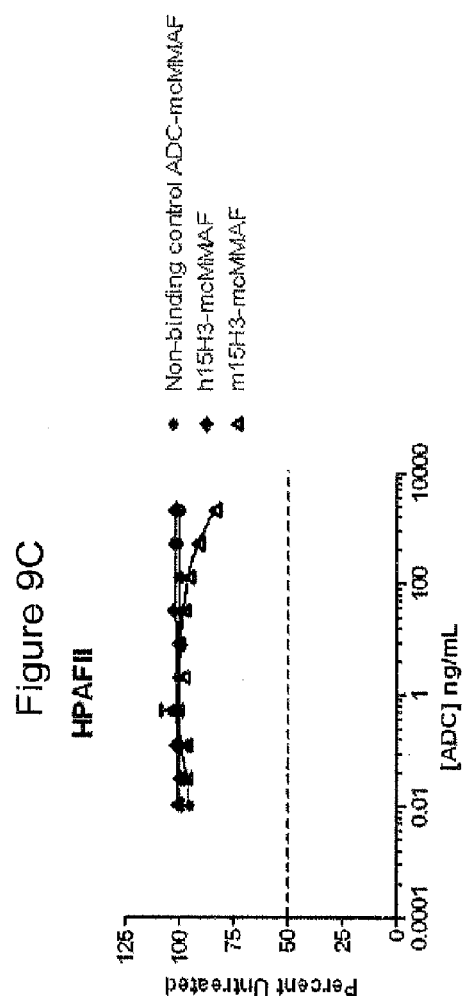
Figure 9C
Figure 9D
Figures 9C-9D

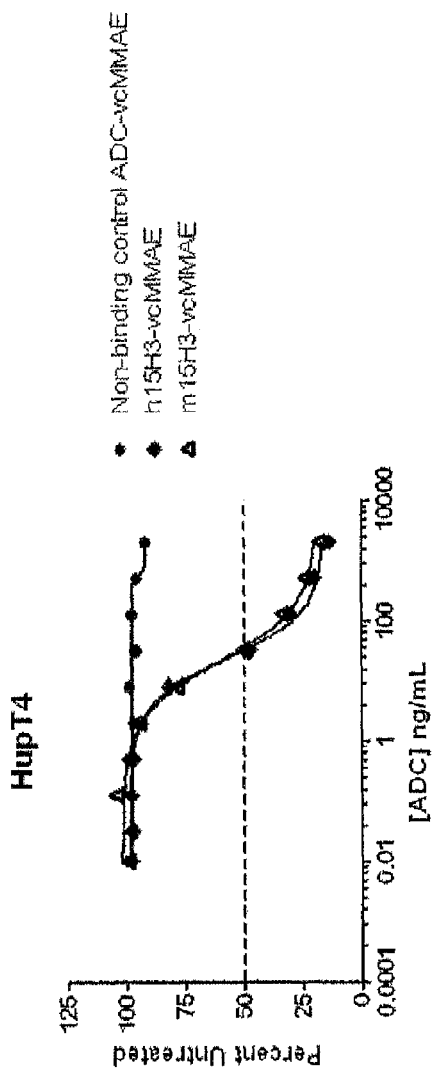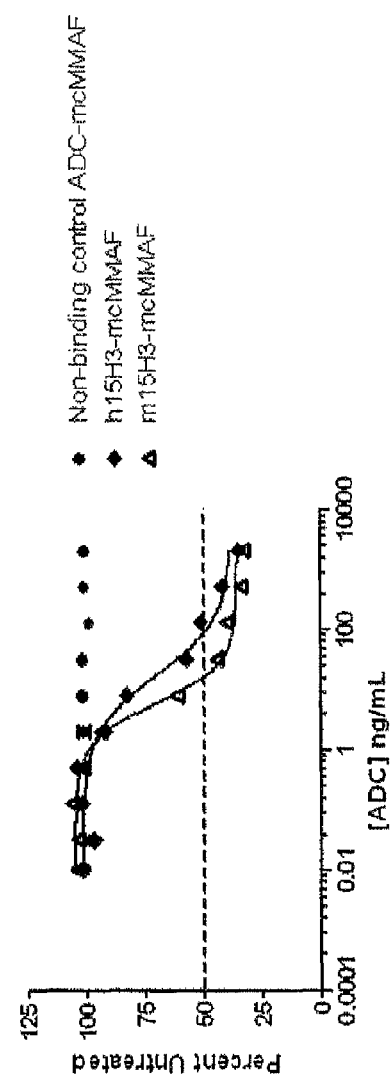
Figure 9E
Figure 9F
Figures 9E-9F

ANTIBODIES TO INTEGRIN AVB6 AND USE OF SAME TO TREAT CANCER

This application is the national stage filing under 35 U.S.C. §371 of International Application No. PCT/US2013/026087 filed Feb. 14, 2013, which claims the benefit of U.S. Provisional Application No. 61/600,499, filed Feb. 17, 2012 and U.S. Provisional Application No. 61/602,511 filed Feb. 23, 2012, each of which is incorporated by reference in its entirety for all purposes.

BRIEF SUMMARY

Provided herein are monoclonal antibodies that specifically bind to integrin αvβ6, and methods of using them to treat cancer. The antibodies described herein include 15H3 antibodies. The 15H3 antibody is a murine monoclonal antibody comprising a heavy chain variable region comprising the amino acid sequence of SEQ ID NO:1 and a light chain variable region comprising the amino acid sequence of SEQ ID NO:2. Chimeric and humanized forms of the 15H3 murine antibody are encompassed by the present invention, as well as human forms thereof. The chimeric, humanized, and human forms of the 15H3 antibody comprise substantially the same complementarity determining regions (CDRs) as the murine 15H3 antibody and specifically bind to integrin αvβ6. The three heavy chain variable region CDRs of the murine 15H3 antibody have the sequences as provided in SEQ ID NO:3 (H-CDR1), SEQ ID NO:4 (H-CDR2), and SEQ ID NO:5 (H-CDR3). The three light chain CDRs of the murine 15H3 antibody have the sequences as provided in SEQ ID NO:6 (L-CDR1), SEQ ID NO:7 (L-CDR2), and SEQ ID NO:8 (L-CDR3). Optionally, in a humanized antibody comprising substantially the same complementarity determining regions (CDRs) as the murine 15H3 antibody that specifically binds to αvβ6, at least one of positions H28, H30, H72, H73, H75, H78, or H93 of the heavy chain variable region is occupied by the amino acid residue from the corresponding position of the murine 15H3 antibody. Optionally in any such antibody, at least two of positions H28, H30, H72, H73, H75, H78, or H93 are occupied by the amino acid residue from the corresponding position of the murine 15H3 antibody. Optionally in any such antibody, at least four of positions H28, H30, H72, H73, H75, H78, or H93 are occupied by the amino acid residue from the corresponding position of the murine 15H3 antibody. Optionally in any such antibody, at least one of positions H28 and H30 are occupied by S. Optionally, in any such antibody, positions H28 and H30 are occupied by S. Optionally, in any such antibody, positions H28 and H30 are occupied by S; position H72 is occupied by D or Q; position H73 is occupied by T or K, position H75 is occupied by T or S; position H78 is occupied by V or A, and position 93 is occupied by A or V. Optionally in any of these embodiments, not more than 10, not more than 9, not more than 8, not more than 7, not more than 6, or not more than 5 of the amino acid residues in the heavy chain framework region are occupied by the amino acid residue from the corresponding position of the murine 15H3 antibody. Optionally, in any of these embodiments, the CDRs of the heavy chain variable region are those of SEQ ID NO:1 and the CDRs of the light chain variable region are those of SEQ ID NO:2. Optionally, in any of these embodiments, the CDRs of the heavy chain variable region are substantially those of SEQ ID NO:1 and the CDRs of the light chain variable region are substantially those of SEQ ID NO:2. Optionally, in any of these embodiments, the CDRs of the heavy chain variable region are those of SEQ ID NO:1 and the CDRs of the light chain variable region are those of SEQ ID NO:2 having 0, 1, 2 or 3 conservative amino acid substitutions in each CDR. In one aspect, provided herein are chimeric or humanized antibodies that specifically bind integrin αvβ6 comprising heavy chain complementary determining region (CDR) sequences as set forth in SEQ ID NO:3 (CDR1), SEQ ID NO:4 (CDR2), and SEQ ID NO:5 (CDR3), and light chain CDR sequences as set forth in SEQ ID NO:6 (CDR4), SEQ ID NO:7 (CDR5), and SEQ ID NO:8 (CDR6) and having 0, 1, 2 or 3 conservative amino acid substitutions in each CDR. Here, as elsewhere in this application, Kabat numbering is used to describe positions in the heavy and light chain variable regions.

The invention also provides antibodies (e.g., humanized antibodies) comprising a heavy chain variable region having an amino acid sequence at least 90% identical to HA (SEQ ID NO:9) and having a light chain variable region at least 90% identical to LA (SEQ ID NO:10). In some aspects, the invention provides antibodies comprising a heavy chain variable region having an amino acid sequence at least 90% identical to HA (SEQ ID NO:9) having at least one murine 15H3 backmutation in the heavy chain variable framework region and a light chain variable region at least 90% identical to LA (SEQ ID NO:10). By the phrase "having at least one murine 15H3 backmutation in the variable chain framework region," it is meant that at least one of the amino acid residues in the acceptor variable chain framework region is changed to an amino acid residue that is present at the corresponding position in the donor murine 15H3 antibody. Optionally in any such antibody, at least one of positions H28, H30, H72, H73, H75, H78, or H93 is occupied by the amino acid residue from the corresponding position of the murine 15H3 antibody. Optionally in any such antibody, at least two of positions H28, H30, H72, H73, H75, H78, or H93 are occupied by the amino acid residue from the corresponding position of the murine 15H3 antibody. Optionally in any such antibody, at least four of positions H28, H30, H72, H73, H75, H78, or H93 are occupied by the amino acid residue from the corresponding position of the murine 15H3 antibody. Optionally in any such antibody, all of positions H28, H30, H72, H73, H75, H78, or H93 are occupied by the amino acid residue from the corresponding position of the murine 15H3 antibody. Optionally in any such antibody, at least one of positions H28 and H30 is occupied by S. Optionally, in any such antibody, positions H28 and H30 are occupied by S. Optionally, in any such antibody, positions H28 and H30 are occupied by S; position H72 is occupied by D or Q; position H73 is occupied by T or K, position H75 is occupied by T or S; position H78 is occupied by V or A, and position 93 is occupied by A or V. Optionally in any of these embodiments, not more than 10, not more than 9, not more than 8, not more than 7, not more than 6, or not more than 5 of the amino acid residues in the heavy chain framework region are occupied by the amino acid residue from the corresponding position of the murine 15H3 antibody. Optionally, in any of these embodiments, the CDRs of the heavy chain variable region are those of SEQ ID NO:1 and the CDRs of the light chain variable region are those of SEQ ID NO:2. Optionally, in any of these embodiments, the CDRs of the heavy chain variable region are substantially those of SEQ ID NO:1 and the CDRs of the light chain variable region are substantially those of SEQ ID NO:2. Optionally, in any of these embodiments, the CDRs of the heavy chain variable region are those of SEQ ID NO:1 and the CDRs of the light chain variable region are those of SEQ ID NO:2 having 0, 1, 2 or 3 conservative amino acid substitutions in each CDR.

The invention also provides antibodies (e.g., humanized antibodies) comprising a heavy chain variable region having an amino acid sequence at least 90% identical to HB (SEQ ID NO:11), HF (SEQ ID NO:12), HG (SEQ ID NO:13), HK (SEQ ID NO:14), HL (SEQ ID NO:15), HM (SEQ ID NO:16), HN (SEQ ID NO:17), HO (SEQ ID NO:18), HQ (SEQ ID NO:19), HR (SEQ ID NO:20), HS (SEQ ID NO:21), HT (SEQ ID NO:22), or HU (SEQ ID NO:23) and a light chain variable region at least 90% identical to LA (SEQ ID NO:10), LB (SEQ ID NO:24), LC (SEQ ID NO:25), LD (SEQ ID NO:26), LE (SEQ ID NO:27), LF (SEQ ID NO:28) or LG (SEQ ID NO:29), and any combinations thereof (i.e., the antibody can comprise any one of the heavy chain variable regions paired with any one of the light chain variable regions). Optionally, the antibody comprises a heavy chain variable region having an amino acid sequence at least 95% identical to HA, HB, HF, HG, HK, HL, HM, HN, HO, HQ, HR, HS, HT, HU and a light chain variable region at least 95% identical to LA, LB, LC, LD, LE, LF, or LG, and any combinations thereof (i.e., the antibody can comprise any one of the heavy chain variable regions paired with any one of the light chain variable regions). Optionally in any such antibody, at least one of positions H28, H30, H72, H73, H75, H78, or H93 is occupied by the amino acid residue from the corresponding position of the murine 15H3 antibody. Optionally in any such antibody, at least two of positions H28, H30, H72, H73, H75, H78, or H93 is occupied by the amino acid residue from the corresponding position of the murine 15H3 antibody. Optionally, in any such antibody, at least one of positions H28 and H30 are occupied by S. Optionally, in any such antibody, positions H28 and H30 are occupied by S. Optionally, in any such antibody, positions H28 and H30 are occupied by S; position H72 is occupied by D or Q; position H73 is occupied by T or K, position H75 is occupied by T or S; position H78 is occupied by V or A, and position 93 is occupied by A or V. Optionally in any of these embodiments, not more than 10, not more than 9, not more than 8, not more than 7, not more than 6, or not more than 5 of the amino acid residues in the heavy chain framework region are occupied by the amino acid residue from the corresponding position of the murine 15H3 antibody. Optionally, in any of these embodiments, the CDRs of the heavy chain variable region are those of SEQ ID NO:1 and the CDRs of the light chain variable region are those of SEQ ID NO:2. Optionally, in any of these embodiments, the CDRs of the heavy chain variable region are substantially those of SEQ ID NO:1 and the CDRs of the light chain variable region are substantially those of SEQ ID NO:2. Optionally, in any of these embodiments, the CDRs of the heavy chain variable region are those of SEQ ID NO:1 and the CDRs of the light chain variable region are those of SEQ ID NO:2 having 0, 1, 2 or 3 conservative amino acid substitutions in each CDR. The heavy chain variable region and light chain variable region of the antibodies described herein are optionally fused to a signal peptide. An exemplary heavy chain murine signal peptide is set forth in SEQ ID NO:33; an exemplary heavy chain human signal peptide is set forth in SEQ ID NO:34; an exemplary light chain murine signal peptide is set forth in SEQ ID NO:35; and an exemplary light chain human signal peptide is set forth in SEQ ID NO:36.

The heavy chain variable region of the antibodies described herein are optionally fused to a heavy chain constant region and the light chain variable region is optionally fused to a light chain constant region. The heavy chain constant region can be a natural human constant region or can be a mutant form of natural human constant region, e.g., one which has reduced binding to an Fcgamma receptor relative to the natural human constant region. Optionally, the heavy chain constant region is of IgG1 isotype. Optionally, the heavy chain constant region has an amino acid sequence comprising SEQ ID NO:30 and the light chain constant region has an amino acid sequence comprising SEQ ID NO:31. Optionally, the heavy chain constant region has an amino acid sequence comprising SEQ ID NO:32 and the light chain constant region has an amino acid sequence comprising SEQ ID NO:31. Optionally, the antibody is conjugated to a cytotoxic agent (i.e., antibody-drug conjugate). Certain antibodies of the present invention have an affinity for human αvβ6 that is greater than the murine version of the 15H3 antibody. Some other antibodies have an affinity for human αvβ6 that is no more than 10 times lower, preferably not more than 6 times lower, more preferably no more than 5 times lower, even more preferably no more than 2 times lower than the murine version of the 15H3 antibody as determined by a competition binding assay or saturation binding assay (such as the ones described in the examples). In some aspects, humanized antibodies described herein have an affinity for human αvβ6 that is within about 10 fold, preferably within about 5 fold, more preferably within about 2 fold, the affinity of the murine 15H3 antibody for human αvβ6. In some aspect, the humanized antibodies described herein have an apparent dissociation constant (kd) for human αvβ6 within a range of 0.1 nM to 10 nM, preferably 0.1 nM to 5 nM, more preferably 0.1 nM to 2 nM, 0.5 nM to 2 nM or 0.5 nM to 1.5 nM.

Also provided are bispecific monoclonal antibodies comprising amino acid sequences described herein.

The invention further provides nucleic acids encoding a heavy chain variable region and/or a light chain variable region of any of the antibodies described above.

The invention further provides a method of treating a patient having cancer, comprising administering to the patient an effective regime of an antibody as described above. Preferably the antibody is conjugated to a cytotoxic agent. The cancer is one that expresses the αvβ6 antigen. Optionally, the cancer is bladder cancer, head and neck cancer (including cancers of the lip, oral cavity, nasal cavity, paranasal sinuses, pharynx, and larynx), skin cancer, lung cancer, pancreatic cancer, uterine cancer, breast cancer (including triple negative breast cancer), cervical cancer, colon cancer, prostate cancer, ovarian cancer, gastric cancer, or liver cancer. Optionally the cancer is a squamous cell carcinoma or adenocarcinoma.

BRIEF DESCRIPTION OF THE FIGURES

FIG. 1 shows an alignment of the amino acid sequences of the parental murine mAb (referred to as 15H3) with select humanized 15H3 heavy (upper two panels) and light chain variable (lower two panels) regions.

FIGS. 9A-9F show that humanized 15H3 anti-αvβ6 ADCs behaved similarly as the mouse parental in cytotoxicity assays.

DETAILED DESCRIPTION

Figure 2:
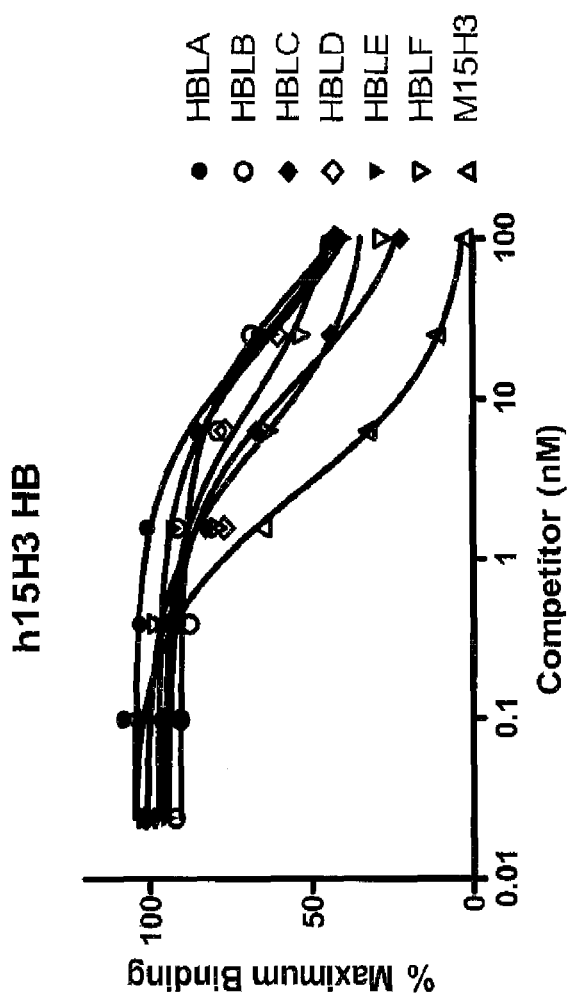
FIG. 2 shows the results of competition binding studies on 293F cells expressing human αvβ6 with antibodies having the HB heavy chain and the parental murine antibody (referred to as m15H3).
Figures 3A, 3B, 3C:
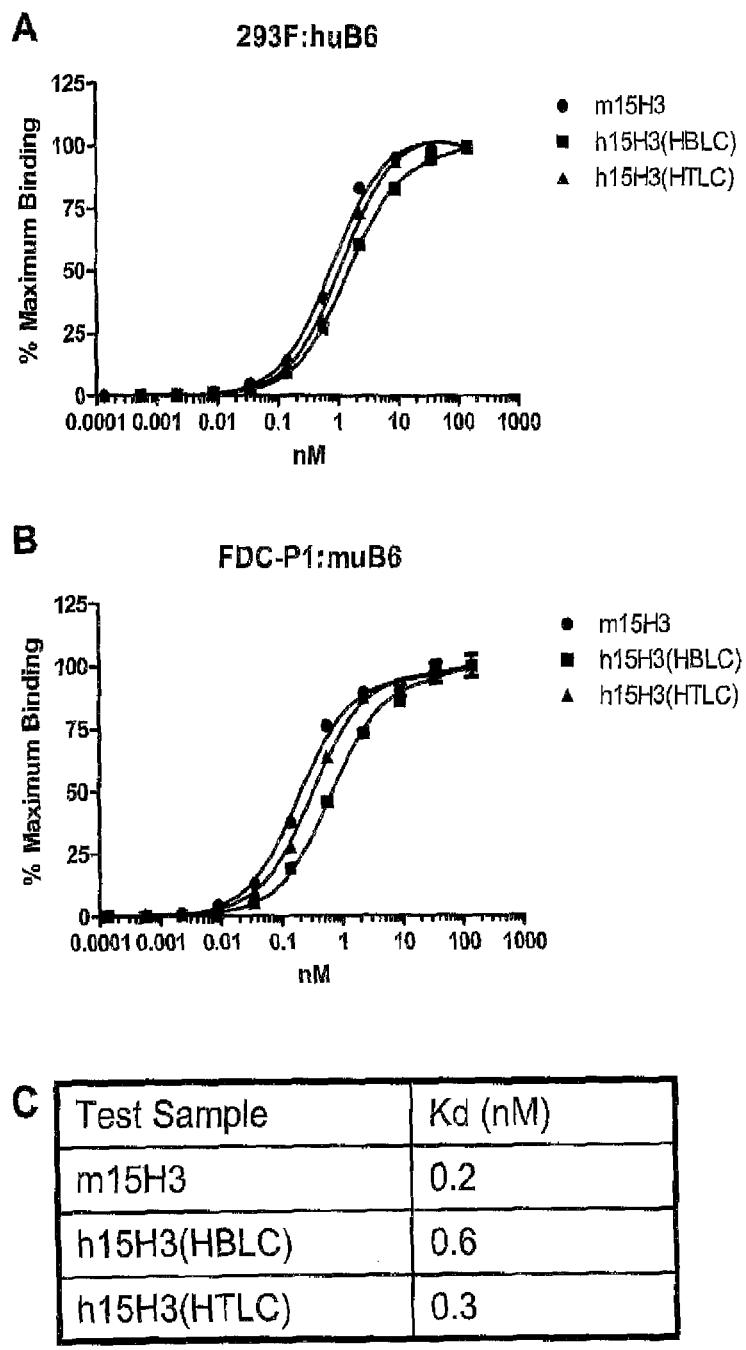
FIGS. 3A-C show the results of saturation binding studies on 293F cells and FDC-P1 cells expressing αVβ6 with antibodies HBLC and HTLC.
Figure 4:
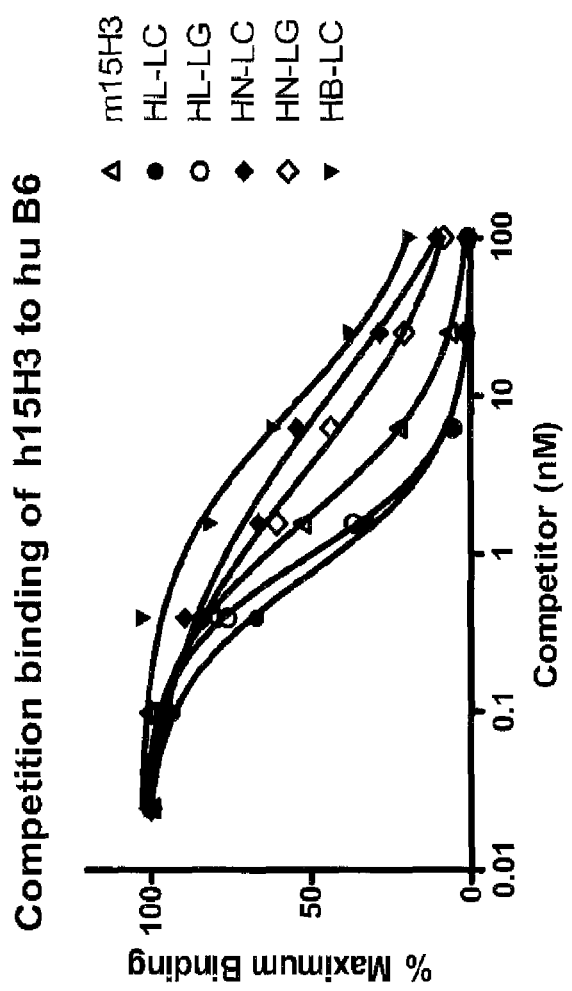
FIG. 4 shows the results of competition binding studies on 293F cells expressing αvβ6 with antibodies having the HB, HL, and HN heavy chains and the parental murine antibody (referred to as m15H3).
Figure 5:
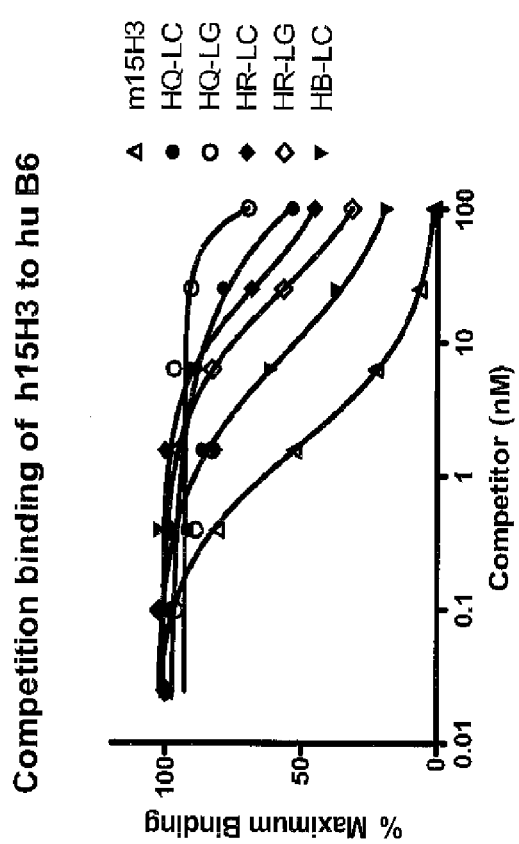
FIG. 5 shows the results of competition binding studies on 293F cells expressing αvβ6 with antibodies having the HB, HQ, and HR heavy chains and the parental murine antibody (referred to as m15H3).
Figure 6:
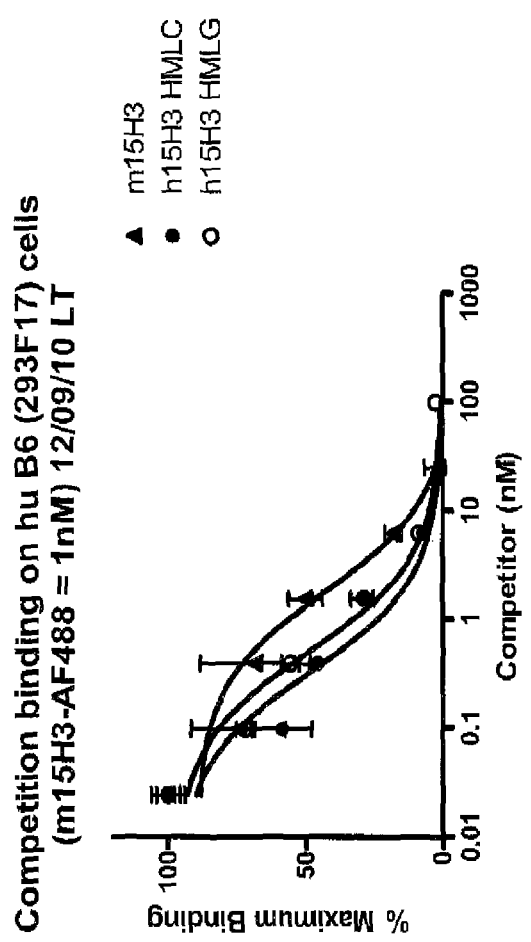
FIG. 6 shows the results of competition binding studies on 293F cells expressing αvβ6 with antibodies having the HM heavy chains and the parental murine antibody (referred to as m15H3).
Figure 7:
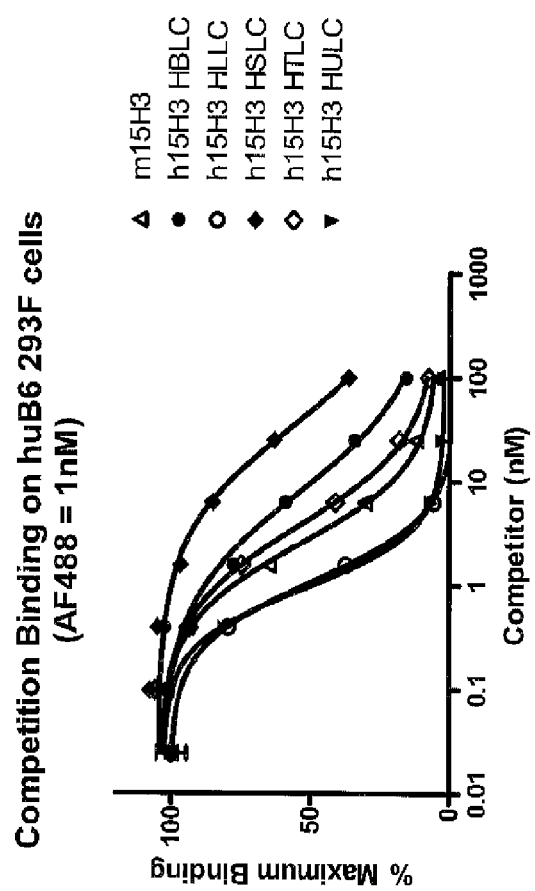
FIG. 7 shows the results of competition binding studies on 293F cells expressing αvβ6 with antibodies having the HB, HL, HS, HT, and HU heavy chains and the parental murine antibody (referred to as m15H3).
Figure 8:
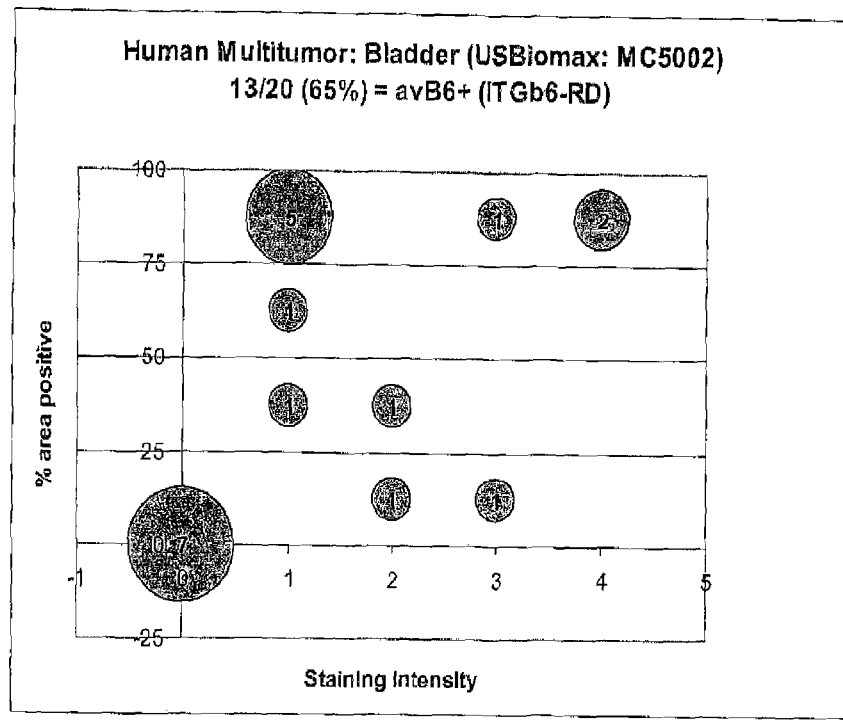
FIG. 8 shows an analysis of αvβ6 protein expression by IHC on bladder cancer samples from a Tumor Micro Array.

The invention provides, inter alia, monoclonal antibodies that specifically bind to αvβ6 and conjugates thereof. The antibodies are useful for treatment and diagnoses of conditions associated with αvβ6 expression (including various cancers) as well as for detecting αvβ6. Antibodies that specifically bind to αvβ6 specifically bind to the β6 integrin subunit alone and/or the αvβ6 integrin complex but not the αv subunit alone.

An "isolated" antibody refers to an antibody that has been identified and separated and/or recovered from components of its natural environment and/or an antibody that is recombinantly produced. A "purified antibody" is an antibody that is typically at least 50% w/w pure of interfering proteins and other contaminants arising from its production or purification but does not exclude the possibility that the antibody is combined with an excess of pharmaceutical acceptable carrier(s) or other vehicle intended to facilitate its use. Interfering proteins and other contaminants can include, for example, cellular components of the cells from which an antibody is isolated or recombinantly produced. Sometimes antibodies are at least 60%, 70%, 80%, 90%, 95 or 99% w/w pure of interfering proteins and contaminants from production or purification. The antibodies described herein, including murine, chimeric, humanized, and human antibodies can be provided in isolated and/or purified form.

The term "monoclonal antibody" as used herein refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256:495, or may be made by recombinant DNA methods (see, for example, U.S. Pat. No. 4,816,567). The "monoclonal antibodies" may also be isolated from phage antibody libraries using the techniques described in Clackson et al. (1991) *Nature,* 352:624-628 and Marks et al. (1991) *J. Mol. Biol.,* 222:581-597, for example or may be made by other methods. The antibodies described herein are monoclonal antibodies.

Specific binding of a monoclonal antibody to its target antigen means an affinity of at least $10^6$, $10^7$, $10^8$, $10^9$, or $10^{10}$ M$^{-1}$ and is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Antibodies can be assayed for specific binding to αvβ6 by known methods, such as for example, competitive and non-competitive immunoassay systems using techniques such as Western blots, radioimmunoassays, ELISA (enzyme linked immunosorbent assay), "sandwich" immunoassays, or immunoprecipitation assays.

The basic antibody structural unit of an intact antibody is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N. Y., 1989, Ch. 7, incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

The term "antibody" includes intact antibodies and antigen binding fragments thereof. Typically, antibody fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)). The term "antibody" includes an antibody by itself (naked antibody) or an antibody conjugated to a cytotoxic agent.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., Cancer Res. 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "patient" includes human and other mammalian subjects that receive either therapeutic treatment.

The terms "treatment" or "treat" refer to slowing, stopping, or reversing the progression of a αvβ6-expressing cancer in a patient, as evidenced by a decrease or elimination of a clinical or diagnostic symptom of the disease, by administration of an anti-αvβ6 antibody or antibody-drug conjugate to the subject after the onset of the clinical or diagnostic symptom of the αvβ6-expressing cancer at any clinical stage. Treatment can include, for example, a decrease in the severity of a symptom, the number of symptoms, or frequency of relapse.

For purposes of classifying amino acids substitutions as conservative or nonconservative, the following amino acid substitutions are considered conservative substitutions: serine substituted by threonine, alanine, or asparagine; threonine substituted by proline or serine; asparagine substituted by aspartic acid, histidine, or serine; aspartic acid substituted by glutamic acid or asparagine; glutamic acid substituted by glutamine, lysine, or aspartic acid; glutamine substituted by arginine, lysine, or glutamic acid; histidine substituted by tyrosine or asparagine; arginine substituted by lysine or glutamine; methionine substituted by isoleucine, leucine or valine; isoleucine substituted by leucine, valine, or methionine; leucine substituted by valine, isoleucine, or methionine, phenylalanine substituted by tyrosine or tryptophan; tyrosine substituted by tryptophan, histidine, or phenylalanine; proline substituted by threonine; alanine substituted by serine; lysine substituted by glutamic acid, glutamine, or arginine; valine substituted by methionine, isoleucine, or leucine; and tryptophan substituted by phenylalanine or tyrosine.

Percentage sequence identities are determined with antibody sequences maximally aligned by the Kabat numbering convention. After alignment, if a subject antibody region (e.g., the entire variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Designation of a range of values includes all integers within or defining the range.

An antibody effector function refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the αvβ6 targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRI (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by CD 16$^+$ effector cells through the secretion of membrane pore-forming proteins and proteases, while phagocytosis is mediated by CD32$^+$ and CD64$^+$ effector cells (see *Fundamental Immunology*, 4$^{th}$ ed., Paul ed., Lippincott-Raven, N. Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6$^{th}$ ed., Janeway et al., Garland Science, N. Y., 2005, Chapter 2).

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytotoxic effect" refers to the depletion, elimination and/or the killing of a target cell. A "cytostatic effect" refers to the inhibition of cell proliferation. A "cytotoxic agent" as used herein refers to an agent that has a cytotoxic and/or cytostatic effect on a cell. Cytotoxic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-αvβ6 antibody is delivered.

The phrase "pharmaceutically acceptable salt," refers to pharmaceutically acceptable organic or inorganic salts of an anti-αvβ6 antibody or conjugate thereof or agent administered with an anti-αvβ6 antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, the term "about" encompasses values within a standard deviation of a stated value.

I. Target Molecules

Unless otherwise indicated, αvβ6 means human αvβ6. An exemplary β6 human sequence is assigned GenBank accession number AAA36122. An exemplary αv human sequence is assigned NCBI NP_002201.1

II. Antibodies of the Invention

A. Binding Specificity and Functional Properties

The invention provides the murine 15H3 antibody and chimeric, humanized, and human 15H3 antibodies.

The affinity of antibodies of the present invention (e.g., chimeric, humanized and human forms of the mouse 15H3 antibody) for human αvβ6 is preferably equivalent to the affinity of mouse 15H3 antibody for human αvβ6, greater than the affinity of mouse 15H3 antibody for human αvβ6 or within a factor of ten, within a factor of five, or within a factor of two weaker than that of the murine antibody 15H3 for human αvβ6 e.g., preferably not more than 10 times weaker, more preferably not more than 5 times weaker and even more preferably not more than 2 times weaker than the affinity of mouse 15H3 antibody for human αvβ6. One method of measuring affinity of an antibody for its target antigen is by determining an antibody's apparent dissociation constant. The present invention encompasses antibodies (e.g., chimeric, humanized and human forms of the mouse 15H3 antibody) having an apparent dissociation constant that is essentially the same as that of murine 15H3 (i.e., within experimental error) as well as antibodies having an dissociation constant lower or higher than that of murine antibody 15H3 for human αvβ6. In some embodiments, antibodies of the present invention (e.g., chimeric, humanized and human forms of the mouse 15H3 antibody) have an apparent dissociation constant within a range of 0.1 to 10 times, or preferably within a range of 0.1 to 5 times, 0.1 to 2 times, or even 0.5 to 2 times that of the apparent dissociation constant of the murine 15H3 antibody for human αvβ6. In some aspects, the apparent dissociation constant (kd) of the antibodies for human αvβ6 is preferably within a range of 0.1 nM to 5 nM, even more preferably within a range of 0.1 nM to 5 nM, even preferably within a range of 0.1 nM to 2 nM or 0.5 nM to 1.5 nM. Chimeric, humanized and human 15H3 antibodies specifically bind to human αvβ6 in native form and/or recombinantly expressed from CHO cells as does the mouse 15H3 antibody. Typically, chimeric, humanized and human 15H3 anti-αvβ6 antibodies compete with murine 15H3 for binding to human αvβ6.

Preferred antibodies inhibit cancer (e.g., growth of cells, metastasis and/or lethality to the organisms) alone (i.e., as a naked antibody) or when conjugated to a cytotoxic agent as shown on cancerous cells propagating in culture, in an animal model or clinical trial. Animal models can be formed by implanting αvβ6 expressing human tumor cell lines into appropriate immunodeficient rodent strains, e.g., athymic nude mice or SCID mice. These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-αvβ6 antibodies or conjugated forms thereof as described in the Examples.

B. Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a human antibody sequence, a composite of such sequences, a consensus sequence of human antibody sequences, or a germline region sequence. A preferred acceptor sequence for the heavy chain is the germline $V_H$ exon $V_H$1-46 and for the J exon ($J_H$), exon $J_H$-4. For the light chain, a preferred acceptor sequence is exon VK2-30 (also referred to in the literature as KV2-30) and for the J exon Jκ-2. Alternative preferred acceptor sequences for the heavy chain include the germline $V_H$ exons $V_H$1-8 or VH1-3 with the J exons ($J_H$), $J_H$-1, $J_H$-4, or $J_H$-5. Alternative preferred acceptor sequences for the light chain include exon VK2-29 (also referred to in the literature as KV2-30) with J exons Jκ-1, Jκ-2, Jκ-3, Jκ-4, or Jκ-5. Thus, a humanized antibody is an antibody having some or all CDRs entirely or substantially from a non-human donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. In some aspects, a humanized antibody comprises a humanized heavy chain and a humanized light chain. A CDR in a humanized or human antibody is substantially from or substantially identical to a corresponding CDR in a non-human antibody when at least 60%, 85%, 90%, 95% or 100% of corresponding residues (as defined by Kabat) are identical between the respective CDRs. In some embodiments, a CDR in a humanized antibody or human antibody is substantially from or substantially identical to a corresponding CDR in a non-human antibody when there are no more than 3 conservative amino acid substitutions in each CDR. The variable region framework sequences of an antibody chain or the constant region of an antibody chain are substantially from a human variable region framework sequence or human constant region respectively when at least 70%, 80%, 85%, 90%, 95% or 100% of corresponding residues defined by Kabat are identical. In some humanized antibodies of the present invention, there is at least one murine 15H3 backmutation in the heavy chain variable framework region of the antibody.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region); or
(4) mediates interaction between the heavy and light chains.

Although the 15H3 antibody was identified as a mouse antibody, the present application also encompasses human 15H3 antibodies. By the term, "human 15H3 antibody" is meant an antibody that is derived from human immunoglobulin gene sequences and that has CDRs that are substantially identical to those of murine 15H3 antibody and displays similar properties, i.e., binding specificity to αvβ6. In some aspects, a human 15H3 antibody comprises a heavy chain variable region that is substantially identical to a heavy chain variable region described herein and/or a light chain variable region that is substantially identical to a light chain variable region described herein. In some embodiments, a 15H3 antibody of the present invention is not a human antibody, e.g., a 15H3 antibody of the present invention is a murine, chimeric, or humanized antibody.

The invention provides 15H3 antibodies in which the heavy chain variable region shows at least 90% identity to HA (SEQ ID NO:9) and a light chain variable region at least 90% identical to LA (SEQ ID NO:10). In some aspects, the antibody is a humanized antibody and there is at least one murine 15H3 backmutation in the heavy chain variable framework region. Additionally, the invention provides 15H3 antibodies in which the humanized heavy chain variable region shows at least 90%, 95% or 99% sequence identity to SEQ ID NOS: 11-23 and the humanized light chain variable region shows at least 90%, 95% or 99% sequence identity to SEQ ID NOS: 10 and 24-29 (and any combinations thereof. The invention provides antibodies in which the heavy chain variable region shows at least 90%, 95% or 99% or 100% sequence identity to SEQ ID NOS: 11, 12, 13, 14, 15, 16, 17, 18, 19, 20, 21, 22, or 23, and the humanized light chain variable region shows at least 90%, 95% or 99% or 100% sequence identity to SEQ ID NO:10. In another embodiment, the invention provides antibodies in which the heavy chain variable region shows at least 90%, 95% or 99% or 100% sequence identity to SEQ ID NOS: 11, 12, 13, 14, 15, 16, 17, 18, 19, 20, 21, 22, or 23, and the light chain variable region shows at least 90%, 95% or 99% or 100% sequence identity to SEQ ID NO:24. In another embodiment, the invention provides antibodies in which the heavy chain variable region shows at least 90%, 95% or 99% or 100% sequence identity to SEQ ID NOS: 11, 12, 13, 14, 15, 16, 17, 18, 19, 20, 21, 22, or 23, and the light chain variable region shows at least 90%, 95% or 99% or 100% sequence identity to SEQ ID NO:25. In another embodiment, the invention provides antibodies in which the heavy chain variable region shows at least 90%, 95% or 99% or 100% sequence identity to SEQ ID NOS: 11, 12, 13, 14, 15, 16, 17, 18, 19, 20, 21, 22, or 23, and the light chain variable region shows at least 90%, 95% or 99% or 100% sequence identity to SEQ ID NO:26. In another embodiment, the invention provides antibodies in which the heavy chain variable region shows at least 90%, 95% or 99% or 100% sequence identity to SEQ ID NOS: 11, 12, 13, 14, 15, 16, 17, 18, 19, 20, 21, 22, or 23, and the light chain variable region shows at least 90%, 95% or 99% or 100% sequence identity to SEQ ID NO:27. In another embodiment, the invention provides antibodies in which the heavy chain variable region shows at least 90%, 95% or 99% or 100% sequence identity to SEQ ID NOS: 11, 12, 13, 14, 15, 16, 17, 18, 19, 20, 21, 22, or 23, and the light chain variable region shows at least 90%, 95% or 99% or 100% sequence identity to SEQ ID NO:28. In another embodiment, the invention provides antibodies in which the heavy chain variable region shows at least 90%, 95% or 99% or 100% sequence identity to SEQ ID NOS: 11, 12, 13, 14, 15, 16, 17, 18, 19, 20, 21, 22, or 23, and the light chain variable region shows at least 90%, 95% or 99% or 100% sequence identity to SEQ ID NO:29. In some aspects, these antibodies are humanized antibodies and some or all of the backmutations in the respective antibodies are retained. In other words, in such antibodies, preferably, at least one of positions H28, H30, H72, H73, H75, H78, or H93 is occupied by the amino acid from the corresponding position of the murine 15H3 antibody. Optionally, in any such antibody, at least one of positions H28 and H30 are occupied by S. Optionally, in any such antibody, positions H28 and H30 are occupied by S. Optionally, in any such antibody, positions H28 and H30 are occupied by S; position H72 is occupied by D or Q; position H73 is occupied by T or K, position H75 is occupied by T or S; position H78 is occupied by V or A, and position 93 is occupied by A or V. Preferably, in any of the antibodies described about, e.g., 15H3 humanized antibodies in which the heavy chain variable region shows at least 90%, 95% or 99% sequence identity to SEQ ID NOS: 11-23 and the light chain variable region shows at least 90%, 95% or 99% sequence identity to SEQ ID NOS: 10 and 24-29, the CDR regions are identical or substantially identical to the CDR regions of the mouse donor antibody, i.e., murine 15H3 antibody (SEQ ID NO:3-8). The CDR regions are as defined by Kabat. Antibodies of the present invention include antibodies HBLA, HBLB, HBLC, HBLD, HBLE, HBLF, HBLG, HLLA, HLLB, HLLC, HLLD, HLLE, HLLF, HLLG, HMLA, HMLB, HMLC, HMLD, HMLE, HMLF, HMLG, HNLA, HNLB, HNLC, HNLD, HNLE, HNLF, HNLG, HRLA, HRLB, HRLC, HRLD, HRLE, HRLF, HRLG, HSLA, HSLB, HSLC, HSLD, HSLE, HSLF, HSLG, HTLA, HTLB, HTLC, HTLD, HTLE, HTLF, HTLG, HULA, HULB, HULC, HULD, HULE, HULF, and HULG.

Another possible variation is to substitute certain residues in the CDRs with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196: 901, 1987), by molecular modeling and/or empirically, or as described in Gonzales et al., Mol. Immunol. 41: 863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence or a conservative substitution. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity.

In preferred embodiments herein, the CDR regions of the humanized and human 15H3 antibodies are identical or substantially identical to the CDR regions of the murine 15H3 antibody (SEQ ID NO:3-8). In any of the antibodies described herein, the CDR regions can be those of the murine 15H3 antibody (i.e., SEQ ID NO:3-8) with 0, 1, 2 or 3 conservative amino acid substitions. In any of the antibodies described herein, the CDR regions can be those of the murine 15H3 antibody (i.e., SEQ ID NO:3-8) with 0, 1, 2 or 3 conservative amino acid substitutions in each CDR. In any of the antibodies described herein, the CDR regions can be those of the murine 15H3 antibody (i.e., SEQ ID NO:3-8) with 0, 1, 2 or 3 conservative amino acid substitutions in CDR1 and CDR2 of the heavy chain and CDR1, CDR2 and optionally CDR3 of the light chain. By molecular modeling and empirical deduction, it has been determined that in any of the antibodies described herein, the conservative amino acid substition can be, for example, at position 24, 25, 32, 33, and/or 34 in CDR1 of the light chain, positions 53-56 in CDR2 of the light chain, position 31 and/or 32 in CDR1 of the heavy chain, and/or positions 61-65 in CDR2 of the heavy chain. Additionally, in any of the antibodies described herein, the following three positions could be replaced by the corresponding human amino acid: lysine at position 64 in CDR2 of the heavy chain can be replaced by glutamine, lysine at position 24 in CDR1 of the light chain can be replaced by arginine, and leucine at position 54 in CDR2 of the light chain can be replaced by arginine.

C. Selection of Constant Region

The heavy and light chain variable regions of antibodies described herein can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue at amino acid position 234, 235, 237, 239, 267, 298, 299, 326, 330, or 332, preferably an S239C mutation (substitutions of the constant regions are according to the EU index) in a human IgG1 isotype (US 20100158909). The presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (e.g., coupling cytotoxic drugs using thiol specific reagents such as maleimide derivatives of drugs). The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. No. 6,624,821, U.S. Pat. No. 5,624,821.)

The in vivo half-life of an antibody can also impact on its effector functions. The half-life of an antibody can be increased or decreased to modify its therapeutic activities. FcRn is a receptor that is structurally similar to MHC Class I antigen that noncovalently associates with β2-microglobulin. FcRn regulates the catabolism of IgGs and their transcytosis across tissues (Ghetie and Ward, 2000, Annu. Rev. Immunol. 18:739-766; Ghetie and Ward, 2002, Immunol. Res. 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, Ann. Rev. Immunol. 18:739-766; Ghetie and Ward, 2002, Immunol. Res. 25:97-113). The region on human $IgG_1$ involved in FcRn binding has been mapped (Shields et al., 2001, J. Biol. Chem. 276:6591-604). Alanine substitutions at positions Pro238, Thr256, Thr307, Gln311, Asp312, Glu380, Glu382, or Asn434 of human $IgG_1$ enhance FcRn binding (Shields et al., 2001, J. Biol. Chem. 276:6591-604). $IgG_1$ molecules harboring these substitutions have longer serum half-lives. Consequently, these modified $IgG_1$ molecules may be able to carry out their effector functions, and hence exert their therapeutic efficacies, over a longer period of time compared to unmodified $IgG_1$. Other exemplary substitutions for increasing binding to FcRn include a Gln at position 250 and/or a Leu at position 428. EU numbering is used for all position in the constant region.

Oligosaccharides covalently attached to the conserved Asn297 are involved in the ability of the Fc region of an IgG to bind FcγR (Lund et al., 1996, J. Immunol. 157:4963-69; Wright and Morrison, 1997, Trends Biotechnol. 15:26-31). Engineering of this glycoform on IgG can significantly improve IgG-mediated ADCC. Addition of bisecting N-acetylglucosamine modifications (Umana et al., 1999, Nat. Biotechnol. 17:176-180; Davies et al., 2001, Biotech. Bioeng. 74:288-94) to this glycoform or removal of fucose (Shields et al., 2002, J. Biol. Chem. 277:26733-40; Shinkawa et al., 2003, J. Biol. Chem. 278:6591-604; Niwa et al., 2004, Cancer Res. 64:2127-33) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., 2001, J. Biol. Chem. 276:6591-604). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, J. Biol. Chem. 276:6591-604; Okazaki et al., 2004, J. Mol. Biol. 336:1239-49).

Complement fixation activity of antibodies (both C1q binding and CDC activity) can be improved by substitutions at Lys326 and Glu333 (Idusogie et al., 2001, J. Immunol. 166:2571-2575). The same substitutions on a human IgG2 backbone can convert an antibody isotype that binds poorly to C1q and is severely deficient in complement activation activity to one that can both bind C1q and mediate CDC (Idusogie et al., 2001, J. Immunol. 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., 1995, J. Immunol. 154:2226-36). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., 1992, J. Immunol. 148:2918-22). In addition, a bispecific diabody construct with specificity for C1q also confers CDC activity (Kontermann et al., 1997, Nat. Biotech. 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, Ile, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity. Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P311S (see WO 06/036291).

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcgamma receptor binding or increase binding to FcRN.

D. Expression of Antibodies

Chimeric or humanized antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Human antibodies against αvβ6 can be provided by a variety of techniques described below. Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666; use of transgenic mice including human immunoglobulin genes (see, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, *Nature* 148, 1547-1553 (1994), *Nature Biotechnology* 14, 826 (1996), Kucherlapati, WO 91/10741 (1991) and phage display methods (see, e.g. Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332

Once expressed, antibodies can be purified according to standard procedures of the art, including HPLC purification, column chromatography, gel electrophoresis and the like (see generally, Scopes, *Protein Purification* (Springer-Verlag, N Y, 1982)).

III. Nucleic Acids

The invention further provides nucleic acids encoding any of the heavy and light chains described above. Typically, the nucleic acids also encode a signal peptide fused to the heavy and light chains. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector. Exemplary nucleic acids are set forth in SEQ ID NO:37 (murine heavy chain), SEQ ID NO:38 (murine light chain), SEQ ID NO:39 (HA), SEQ ID NO:40 (HB), SEQ ID NO:41 (HL), SEQ ID NO:42 (HT), SEQ ID NO:43 (HN), SEQ ID NO:44 (HU), SEQ ID NO:45 (LA), SEQ ID NO:46 (LC), SEQ ID NO:47 (LF), SEQ ID NO:48 (LG), SEQ ID NO:49 (murine heavy chain signal peptide), SEQ ID NO:50 (human heavy chain signal peptide), SEQ ID NO:51 (murine light chain signal peptide), and SEQ ID NO:52 (human light chain signal peptide). Nucleic acids can be provided in isolated form. An isolated nucleic acid molecule is one that that has been identified and separated and/or recovered from components of its natural environment or one that is non-naturally occurring.

IV. Antibody Drug Conjugates

Anti-αvβ6 antibodies can be conjugated to cytotoxic moieties (including pharmaceutically compatible salts thereof) to form an antibody drug conjugate (ADC). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-αvβ6 antibody can be conjugated to a cytotoxic agent such as a chemotherapeutic agent or a toxin (e.g., a cytostatic or cytocidal agent such as, e.g., abrin, ricin A, pseudomonas exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansinoids (e.g., DM1, DM2, DM3, DM4), taxanes, benzodiazepines, benzodiazepine containing compounds (e.g., pyrrolo[1,4] benzodiazepines, indolinobenzodiazepines, and oxazolidinobenzodiazepines) and vinca alkaloids. Techniques for conjugating therapeutic agents to proteins, and in particular to antibodies, are well-known. (See, e.g., Alley et al., *Current Opinion in Chemical Biology* 2010 14:1-9; Senter, *Cancer J.*, 2008, 14(3):154-169.)

The therapeutic agent (e.g., cytotoxic agent) can be conjugated in a manner that reduces its activity unless it is cleaved off the antibody (e.g., by hydrolysis, by antibody degradation or by a cleaving agent). Such therapeutic agent can be attached to the antibody with a cleavable linker that is sensitive to cleavage in the intracellular environment of the αvβ6-expressing cancer cell but is not substantially sensitive to the extracellular environment, such that the conjugate is cleaved from the antibody when it is internalized by the αvβ6-expressing cancer cell (e.g., in the endosomal or, for example by virtue of pH sensitivity or protease sensitivity, in the lysosomal environment or in the caveolear environment). Such therapeutic agent can also be attached to the antibody with a non-cleavable linker.

Typically the ADC comprises a linker region between the therapeutic agent and the anti-αvβ6 antibody. As noted supra, the linker can be cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. In some aspects, the peptidyl linker is at least two amino acids long or at least three amino acids long. Cleaving agents can include cathepsins B and D and plasmin (see, e.g., Dubowchik and Walker, 1999, *Pharm. Therapeutics* 83:67-123). Most typical are peptidyl linkers that are cleavable by enzymes that are present in αvβ6-expressing cells. For example, a peptidyl linker that is cleavable by the thiol-dependent protease cathepsin-B, which is highly expressed in cancerous tissue, can be used (e.g., a linker comprising a Phe-Leu or a Val-Cit peptide).

The linker also can be a non-cleavable linker, such as, for example, an maleimido-alkylene- or maleimide-aryl linker that is directly attached to the therapeutic agent (e.g., a drug) and released by degradation of the antibody.

Typically, the linker is not substantially sensitive to the extracellular environment meaning that no more than about 20%, typically no more than about 15%, more typically no more than about 10%, and even more typically no more than about 5%, no more than about 3%, or no more than about 1% of the linkers in a sample of the ADC is cleaved when the ADC is present in an extracellular environment (e.g., in plasma). Whether a linker is not substantially sensitive to the extracellular environment can be determined, for example, by incubating independently with plasma both (a) the ADC (the "ADC sample") and (b) an equal molar amount of unconjugated antibody or therapeutic agent (the "control sample") for a predetermined time period (e.g., 2, 4, 8, 16, or 24 hours) and then comparing the amount of unconjugated antibody or therapeutic agent present in the ADC sample with that present in control sample, as measured, for example, by high performance liquid chromatography.

nuclear and cellular division, and have anticancer activity. Typically, the auristatin based antibody-drug conjugate comprises a linker between the auristatin drug and the anti-αvβ6 antibody. The linker can be, for example, a cleavable linker (e.g., a peptidyl linker) or a non-cleavable linker (e.g., linker released by degradation of the antibody). The auristatin can be auristatin E or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other auristatins include MMAF and MMAE. The synthesis and structure of exemplary auristatins are described in U.S. Pat. Nos. 7,659,241, 7,498,298, 2009-0111756, 2009-0018086, and U.S. Pat. No. 7,968,687 each of which is incorporated herein by reference in its entirety and for all purposes.

Exemplary auristatin based antibody drug conjugates include vcMMAE, vcMMAF and mcMMAF antibody drug conjugates as shown below wherein Ab is an antibody as described herein and val-cit represents the valine-citrulline dipeptide:

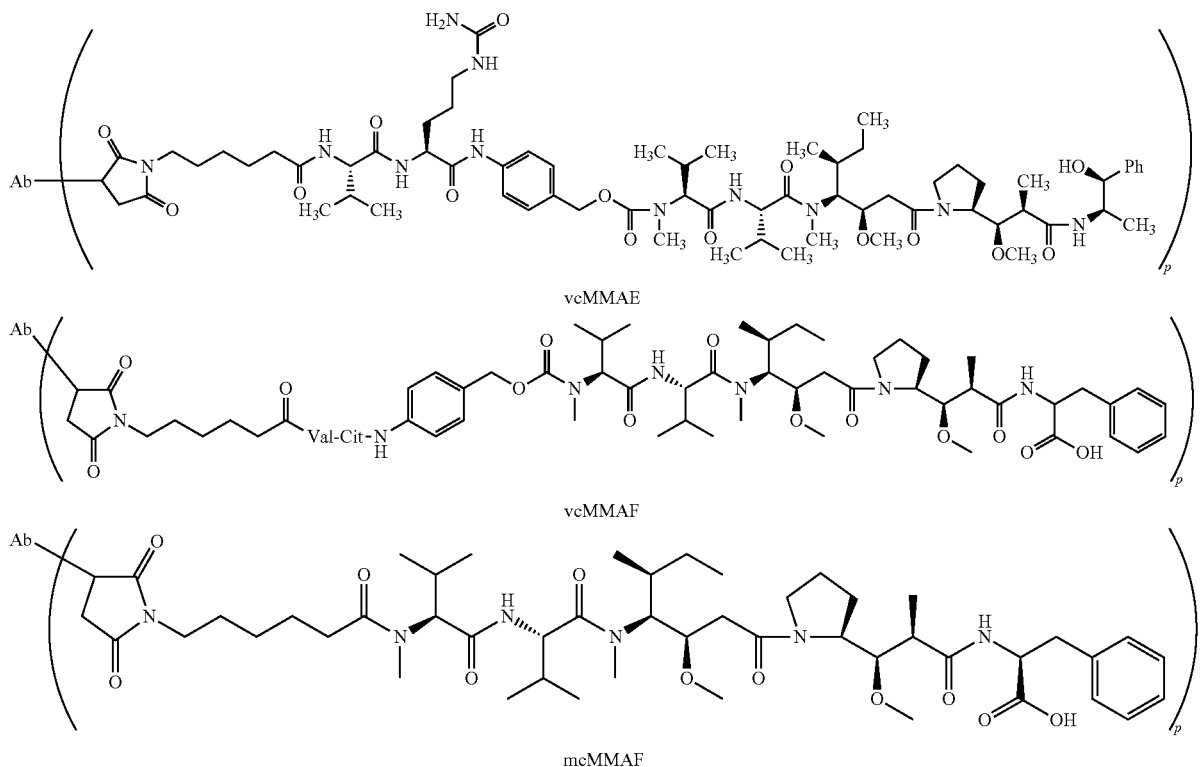

The linker can also promote cellular internalization. The linker can promote cellular internalization when conjugated to the therapeutic agent (i.e., in the milieu of the linker-therapeutic agent moiety of the ADC as described herein). Alternatively, the linker can promote cellular internalization when conjugated to both the therapeutic agent and the anti-αvβ6 antibody (i.e., in the milieu of the ADC as described herein).

Exemplary antibody-drug conjugates include auristatin based antibody-drug conjugates meaning that the drug component is an auristatin drug. Auristatins bind tubulin, have been shown to interfere with microtubule dynamics and or a pharmaceutically acceptable salt thereof. The drug loading is represented by p, the number of drug-linker molecules per antibody. Depending on the context, p can represent the average number of drug-linker molecules per antibody, also referred to the average drug loading. P ranges from 1 to 20 and is preferably from 1 to 8. In some preferred embodiments, when p represents the average drug loading, p ranges from about 2 to about 5. In some embodiments, p is about 2, about 3, about 4, or about 5. The average number of drugs per antibody in a preparation may be characterized by conventional means such as mass spectroscopy, HIC, ELISA assay, and HPLC. In some aspects, the anti-αvβ6 antibody is attached to the drug-linker through a cysteine residue of the antibody. In some aspects, the cysteine residue is one that is engineered into the antibody. In other aspects, the cysteine residue is an interchain disulfide cysteine residue.

V. Other Antibodies to αvβ6

As well as the murine 15H3 antibody and chimeric, humanized, or human forms of the 15H3 antibody, other antibodies binding to an extracellular domain of αvβ6 can be used in some of the methods of the invention, particularly the methods for the treatment of bladder cancer. Preferably, in such embodiments, the antibody is conjugated to a cytotoxic agent. A collection of anti-αvβ6 antibodies are known, see, for example, U.S. Publication Nos. 20100330103 and 20110294982 and U.S. Pat. Nos. 7,465,449; 7,943,742, and 6,692,741, each of which is incorporated by reference herein in its entirety and for all purposes.

Other antibodies to αvβ6 can be made de novo by immunizing with αvβ6 or one or more extracellular domains thereof. The production of other non-human monoclonal antibodies, e.g., murine, guinea pig, primate, rabbit or rat, against an immunogen can be performed by as described by Harlow & Lane, *Antibodies, A Laboratory Manual* (CSHP NY, 1988) (incorporated by reference for all purposes). Such an immunogen can be obtained from a natural source, by peptide synthesis or by recombinant expression.

Humanized, chimeric or veneered forms of non-human antibodies can be made. General methodology for producing humanized antibodies is described by Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). A chimeric antibody is an antibody in which the variable regions of light and heavy chains of a non-human antibody (e.g., a mouse) are combined with human light and heavy chain constant regions. Such antibodies substantially or entirely retain the binding specificity of the mouse antibody, and are about two-thirds human sequence. A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

Human antibodies against αvβ6 can be provided by a variety of techniques as described above.

If desired, any of the antibodies can be selected to have the same or overlapping epitope specificity as an exemplary antibody, such as the 15H3 antibody, by a competitive binding assay or otherwise.

VI. Therapeutic Applications

The antibodies of the invention, alone or as anti-αvβ6 antibody drug conjugates, can be used to treat cancer. Some such cancers show detectable levels of αvβ6 measured at either the protein (e.g., by immunoassay using one of the exemplified antibodies) or mRNA level. Some such cancers show elevated levels of αvβ6 relative to noncancerous tissue of the same type, preferably from the same patient. An exemplary level of αvβ6 on cancer cells amenable to treatment is 1000-200,000 αvβ6 molecules per cell, although higher or lower levels can be treated. Generally, higher copy numbers are preferable for treatment of solid tumors, for example, at least about 15,000 αvβ6 molecules per cell. Optionally, a level of αvβ6 in a cancer is measured before performing treatment.

Examples of cancers associated with αvβ6 expression and amenable to treatment include, for example, bladder cancer, head and neck cancer (including, for example, cancers of the lip, oral cavity, nasal cavity, paranasal sinuses, pharynx, and larynx), skin cancer, lung cancer, pancreatic cancer, uterine cancer, breast cancer (including triple negative breast cancer), colon cancer, prostate cancer, ovarian cancer, stomach cancer, and liver cancer. In one aspect, squamous cell carcinomas and adenocarcinomas are examples of cancers associated with αvβ6 expression and amenable to treatment. The treatment can be applied to patients having primary or metastatic tumors of these kinds. The treatment can also be applied to patients who are treatment naïve, who are refractory to conventional treatments (e.g., hormones, tamoxifen, herceptin), or who have relapsed following a response to such treatments. Anti-αvβ6 antibodies and conjugates thereof can be used to treat cancers that express αvβ6. In one embodiment, a human, humanized or chimeric anti-αvβ6 antibody or conjugate thereof is used treat a subject with a αvβ6-expressing bladder cancer, head and neck cancer (including, for example, cancers of the lip, oral cavity, nasal cavity, paranasal sinuses, pharynx, and larynx), skin cancer, lung cancer, pancreatic cancer, uterine cancer, breast cancer (including triple negative breast cancer), colon cancer, prostate cancer, ovarian cancer, stomach cancer, or liver cancer. In one embodiment, a human, humanized or chimeric anti-αvβ6 antibody or conjugate thereof is used treat a subject with an αvβ6-expressing squamous cell carcinoma or adenocarcinoma.

This application is believed to be the first credible disclosure that αvβ6 protein is expressed on the surface of bladder cancer cells. Thus, αvβ6-directed therapies can be used to treat patients that are afflicted with αvβ6-expressing bladder cancer (e.g., anti-αvβ6 antibodies, peptides, or conjugates thereof). αvβ6-directed therapies for the treatment of bladder cancer includes the antibodies and conjugates disclosed herein, e.g., chimeric, human, and humanized 15H3 antibodies and conjugates thereof, but is not limited to such antibodies or therapies.

Human, humanized or chimeric antibodies, alone or as conjugates thereof, are administered in an effective regime meaning a dosage, route of administration and frequency of administration that delays the onset, reduces the severity, inhibits further deterioration, and/or ameliorates at least one sign or symptom of cancer. The regime can be referred to as a therapeutically effective regime. In some instances, therapeutic efficacy can be observed in an individual patient relative to historical controls or past experience in the same patient. In other instances, therapeutic efficacy can be demonstrated in a preclinical or clinical trial in a population of treated patients relative to a control population of untreated patients.

Exemplary dosages for a monoclonal antibody are, for example, 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. Exemplary dosages for antibody drug conjugates are, for example, 0.01 mg/kg to 10 mg/kg, 0.1 mg/kg to 10 mg/kg, 0.3 mg/kg to 3 mg/kg, 0.5 mg/kg to 3 mg/kg, 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. In some methods, the patient is administered a dose of at least 1.5 mg/kg, at least 2 mg/kg or at least 3 mg/kg, administered once every three weeks or greater. The dosage depends on the identity of the cytotoxic drug, frequency of administration, condition of the patient and response to prior treatment, if any, and whether the disorder is acute or chronic, among other factors.

Administration is typically parenteral, although it need not be. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or conjugate in the circulation, the condition of the patient and the route of administration among other factors. The frequency can be, for example, daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks, or every three weeks, over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. In some aspects, for acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be, for example, 1-100 mg/ml.

Treatment with antibodies and antibody drug conjugates of the invention can be combined with chemotherapy, radiation, stem cell treatment, surgery other treatments effective against the disorder being treated. In some aspects, antibodies and antibody drug conjugates described herein will be administered with other therapies that are standard of care (e.g., front-line standard of care or second or third line treatment or even salvage therapy) for the particular disease to be treated. Useful classes of other agents that can be administered with antibodies and antibody drug conjugates to αvβ6 include, for example, both other targeted therapies and/or non-targeted therapies. Examples include, antibodies or antibody drug conjugates to other receptors expressed on cancerous cells, αvβ6 targeted peptides or conjugates thereof, antitubulin agents (e.g., auristatins), DNA minor groove binders, DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

VII. Other Applications

The anti-αvβ6 antibodies can be used for detecting αvβ6 in the context of clinical diagnosis or treatment or in research. Expression of αvβ6 on a cancer provides an indication that the cancer is amenable to treatment with the antibodies of the present invention. The antibodies can also be sold as research reagents for laboratory research in detecting cells bearing αvβ6 and their response to various stimuli. In such uses, monoclonal antibodies can be labeled with fluorescent molecules, spin-labeled molecules, enzymes or radioisotypes, and can be provided in the form of kit with all the necessary reagents to perform the assay for αvβ6. The antibodies described herein can be used to detect αvβ6 protein expression and determine whether a cancer is amenable to treatment with anti-αvβ6 ADCs. The antibodies can also be used to purify αvβ6, e.g., by affinity chromatography.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Materials

Cell lines described in the following examples were maintained in culture according to the conditions specified by the American Type Culture Collection (ATCC), the National Cancer Institute (NCI) or the Deutsche Sammlung von Mikroorganismen and Zellkulturen GmbH, Braunschweig, Germany (DMSZ). Detroit 562 cell lines, HPAFII cell lines, and BxPC3 cell lines were obtained from ATCC.

FreeStyle™ 293-F (InVitrogen Corp) human epithelial kidney cells and corresponding transfectants were maintained as described by the manufacterer. Cell culture reagents were obtained from Invitrogen Corp. (Carlsbad, Calif.), Molecular Devices (Sunnydale, Calif.) and other suppliers. Secondary antibody reagents were purchased from Jackson ImmunoResearch Laboratories (West Grove, Pa.). Recombinant human $\alpha v\beta 6$ was prepared in house. Recombinant $\alpha v\beta 3$ and $\alpha v\beta 8$ were purchased from R&D Systems (Minneapolis, Minn.). FreeStyle™ 293-F cells express endogenous integrin $\alpha v$ and they were stably transfected with a full length cDNA encoding human, cynomolgus or murine integrin $\beta 6$ to generate HEK293F:hu$\beta 6$, HEK293F:cyno$\beta 6$ and HEK293F:mu$\beta 6$ cell lines, respectively. HEK293F cells transfected with the empty vector (HEK293F:vector) were used as a negative control. Mouse 3T3 and FDC-P1 cells that express endogenous mouse integrin $\alpha v$ were transfected with a full-length cDNA clone for human and mouse integrin $\beta 6$ to generate 3T3:hu$\beta 6$ and FDC-P1:mu$\beta 6$, respectively.

Methodologies:

Saturation Binding Assays

Saturation binding studies were done using the following antigen expressing cell lines: 293F:hu$\beta 6$; 293F:cyno$\beta 6$; FDCP1:mu$\beta 6$ and rat NBT-II. $0.25$-$0.5 \times 10^6$ antigen expressing cells were aliquoted per well into a 96-well v-bottom plate. m15H3, h15H3 (HBLC) and h15H3 (HTLC) were directly labeled with equivalent levels of biotin and added to cells at concentrations ranging from 0.1 pM-150 nM. Cells were incubated on ice for 30 minutes, washed three times in FACS buffer (PBS, 2% fetal bovine serum, 1 mM MgCl$_2$, 1 mM CaCl$_2$, 0.02% NaN$_3$), incubated on ice for 45 minutes with PE conjugated streptavidin (0.5 ug/ml) in FACS buffer, washed three times and resuspended in FACS buffer. Binding was detected using a Becton Dickinson Biosciences FACSCalibur (San Jose, Calif.). The apparent Kd was calculated using GraphPad Software (LaJolla, Calif.).

ELISA 96-well Maxisorb plates (Nunc) were coated overnight at 4° C. with 1 ug/ml of recombinant human $\alpha v\beta 6$, $\alpha v\beta 3$ and $\alpha v\beta 8$ diluted in PBS. Plates were washed in PBS with 0.05% Tween 20 (PBS-T). Wash buffer was removed and plates were blocked for 30 minutes at room temperature in TBS blocking buffer (TBS plus 1 mM MnCl$_2$, 0.05% Tween 20, 1% BSA). Plates were washed and then incubated for 1 hour with biotinylated antibody (m15H3 or h15H3) diluted in TBS blocking buffer at concentrations that ranged from 4.6 ng/ml-10 ug/ml. Plates were washed, incubated for 1 hour with 1 ug/ml of HRP-streptavidin, washed, and then incubated with TMB substrate for 10 minutes. The reaction was stopped with 1 M H$_2$SO$_4$. Absorbance at 450 nm was read using a Fusion HT plate reader (Perkin Elmer, Waltham, Mass.).

Competition Binding Assays

Competition binding assays were done using the 293F:hu$\beta$ and HEK293F:cyno$\beta 6$ cell lines. $1 \times 10^5$ antigen expressing cells were aliquoted in each well of a 96-well v-bottom plate on ice. The cells were incubated for 1 hour with 2 nM AlexaFluor-647 labeled murine 15H3 and increasing concentrations (from 0.024 nM-100 nM) of unlabeled humanized 15H3 constructs. Cells were pelleted and washed 3 times with PBS. The cells were pelleted and resuspended in 125 uL of PBS/BSA. Fluorescence was analyzed by flow cytometry, using percent of saturated fluorescent signal to determine percent labeled murine 15H3 bound and to subsequently extrapolate the EC50 by fitting the data to a sigmoidal dose-response curve with variable slope.

Quantitative Flow Cytometric Analysis

Quantification of $\alpha v\beta 6$ copy number on the cell surfaces was determined using murine $\alpha v\beta 6$ mAb as primary antibody and the DAKO QiFiKit flow cytometric indirect assay as described by the manufacturer (DAKO A/S, Glostrup, Denmark) and evaluated with a Becton Dickinson FACScan flow cytometer.

Cytotoxicity Assay

Tumor cells were incubated with anti-$\alpha v\beta 6$ antibody drug conjugates for 96 hours at 37° C. A non-binding (h00) ADC was used as a negative control. Cell viability was determined using the CellTiter-Glo® luminescent assay (Promega Corporation, Madison, Wis.) and results were measured on a Fusion HT plate reader (Perkin Elmer, Waltham, Mass.). Results are reported as IC$_{50}$, the concentration of compound needed to yield a 50% reduction in viability compared to vehicle-treated cells (control=100%).

Production of Antibody Drug Conjugates

Antibody drug conjugates of the anti-$\alpha v\beta 6$ antibodies were prepared as described in US20050238649. The drug linkers vcMMAE and mcMMAF are both described in US20050238649 incorporated herein by reference for all purposes.

In Vivo Activity Study

Nude (nu/nu) mice (7-10 animals/group) were implanted with tumor cells grown in culture Detroit 562 (ATCC) were implanted using $5 \times 10^5$ cells in 25% matrigel and HPAFII (ATCC) were implanted using $1 \times 10^6$ in 25% matrigel. Dosing with humanized $\alpha v\beta 6$ ADC or nonbinding control ADC started when tumors reached 100 mm$^3$ (q4d×4 intraperitoneal injections). Tumor volumes were monitored using calipers and animals were euthanized when tumor volume reached ~800 mm$^3$. Median tumor volume plots were continued for each group until one or more animals were euthanized. All animal procedures were performed under a protocol approved by the Institutional Animal Care and Use Committee in a facility accredited by the Association for Assessment and Accreditation of Laboratory Animal Care.

Immunohistochemical (IHC) Staining Method

The Multi-Tumor microarrays (TMA) (cat #MC5001) was purchased from US Biomax Inc. All samples were processed on Bond-Max™ auto-stainer (Leica).

IHC Staining of FFPE Tissues:

Slides with paraffin sections from the multi-tumor array block MC5001 were de-paraffinized using Bond™ Dewax solution (Leica, cat # AR9222) at 72° C. and rehydrated. Antigen retrieval was performed using EDTA based Bond™ Epitope Retrieval Solution 2 (Leica, cat # AR9640) for 20 min at 95-100° C. Slides were treated for 30 min with protein block (DAKO cat #X0909) before incubation with the primary antibody murine anti-integrin $\beta 6$ clone 437216 (RnD MAB#41551) at 5 µg/ml for 45 minutes at 25° C. Isotype-matched murine IgG2b (Zymed #02-6300) was used at 5 µg/ml as negative control for background staining. For automated IHC staining an alkaline phosphatase—Fast Red based detection kit (Bond™ Polymer AP Red Detection kit; Leica, cat # DS9305) was used. After chromogen development, sections were counterstained with hematoxylin and coverslipped. Slides were evaluated and scored by a pathologist and images were taken using a Olympus BX41 microscope.

IHC of Frozen Tissues:

Slides with frozen sections were incubated in acetone for 10 minutes at −20° C. in order to fix the tissue. PeroxAbolish (Biocare cat #PXA96) peroxide blocking reagent was applied for 15 minutes at 25° C. to quench endogenous peroxidase. The slides were sequentially incubated in avidin block (Vector cat #SP-2001) followed by biotin block (Vector cat #SP-2001) for 15 minutes each at 25° C. The slides were incubated with the primary antibody humanized anti-integrin β6 clone 15H3 at 10 μg/ml for 60 minutes. The primary and secondary antibodies were prepared in Bond™ Primary Antibody Diluent (Leica cat #AR9352) containing 50 mM MnCl. Human IgG (Ancell cat #295-010) was used at 10 μg/ml as a negative control for background staining. Following primary antibody incubation, a biotinylated goat anti-human secondary antibody (Jackson cat #109-066-098) was used at 5 μg/ml and incubated for 30 minutes at 25° C. For detection of the biotinylated secondary antibody, VECTASTAIN Elite ABC reagent (Vector cat #PK-7100) was applied for 30 minutes at 25° C. The Bond™ Polymer Refine detection kit (Leica cat #DS9800) was used for DAB chromogen development. Sections were counterstained with hematoxylin and coverslipped. Slides were evaluated and scored by a pathologist and images were taken using an Olympus BX41 microscope.

Results

1. Binding of Mouse Antibody

The $K_D$ for the murine αvβ6 monoclonal antibody 15H3 antibody and select humanized version thereof was determined for human, cyno, rat, and mouse. Competition and saturation binding studies for integrin β6 orthologs was done using genetically engineered cell lines (293F:huβ6, 293F:cynoβ6 or FDC-P1:muβ6) with the exception of rat. The genetically engineered cell lines express endogenous αv which pairs with the recombinant β6 chain to produce a heterodimeric receptor composed of endogenous αv and recombinant β6. The affinity for rat αvβ6 was determined using rat NBT-II bladder carcinoma cells, which expression endogenous αvβ6.

TABLE 1

| Species | h15H3 (HTLC) (nM) | h15H3 (HBLC) (nM) | m15H3 (nM) |
|---|---|---|---|
| Human | 1.2 | 1.4 | 0.8 |
| Cyno | 1.5 | 1.6 | 1.0 |
| Rat | 0.4 | No data | 0.2 |
| Mouse | 0.3 | 0.6 | 0.2 |

Generation of 15H3 Antibody

BALB/c mice were immunized three times with intraperitoneal injections of ~5×10$^6$ 3 T3:huβ6 transfectants. Three days prior to fusion, mice received a final injection of purified recombinant human αvβ6 that was given intravenously (6 ug) and intraperitoneally (30 ug). Lymphocytes harvested from spleen and lymph nodes were fused to P3X63Ag8.653 myeloma cells using polyethylene glycol. Fused cells were recovered overnight in hybridoma growth media (IMDM containing 4 mM glutamine, 10% Fetal Clone I, 10% Cloning Factor and Penicillin/Streptomycin). Following recovery, cells were spun down and then plated in semi-solid media. Semi-solid media consisted of CloneMatrix media supplemented with hybridoma growth media plus HAT for hybridoma selection and CloneDetect for IgG-production. Hybridomas were incubated for 10 days at 37° C. At day 10, IgG producing hybridoma clones were picked using a ClonePixFL (Molecular Devices) and transferred to 96-well plates containing IgG-depleted hybridoma growth media plus HT. Hybridoma culture supernatants were screened on 293F:huβ6 transfectants and positive clones were identified using an Alexifluor-647 labeled secondary antibody for detection. The plates were read in an FMAT 8200 (Applied Biosystems). Hybridomas that bound to 293F:huβ6 and 293F:cynoβ6 but not 293F:vector were expanded for direct conjugation. The directly conjugated antibody panel was tested in binding and cytotoxicity assays. m15H3 was selected as the lead antibody because it showed cytotoxic activity as an ADC on multiple αvβ6-positive tumor cell lines and it had comparable affinity to human and cynomolgus forms of the antigen. The specificity of mouse 15H3 and humanized 15H3 was confirmed in FMAT and FACS binding studies where the antibodies were shown to bind to 293F:huβ6 transfectants but not to the αvβ5-positive parental line (293F:vector). The binding specificity of m15H3 and h15H3 was also confirmed by ELISA where the antibodies were bound to recombinant human αvβ6 but not αvβ3 or αvβ8.

Design and Testing of Humanized Antibodies

The starting point or donor antibody for humanization in this example is the murine 15H3 antibody Genomic sequences provided by VH1-46 and JH4 for the heavy chain and by VK2-30 and Jk2 for the light chain were used.

In a first humanization round, thirteen positions were identified in the heavy chain (H28, H30, H38, H40, H41, H48, H66, H67, H69, H71, H72, H93, and H108) and 6 position were identified in the light chain (L21, L22, L36, L37, L45 and L63) at which the human acceptor sequence differed from the donor sequence and that may affect antibody binding as a result of contacting antigen directly, affecting conformation of CDRs or affecting packing between heavy and light chains. Eight humanized heavy chains and five humanized light chains were made incorporating back mutations at different permutations of these positions. Backmutations are underlined and in bold. (Tables 2 and 3). The remainder of the positions are occupied by the residues from the human acceptor sequence.

TABLE 2

Heavy Chain Backmutations

| Ab | H28 | H30 | H38 | H40 | H41 | H48 | H66 | H67 | H69 | H71 | H72 | H93 | H108 | # back mutations |
|---|---|---|---|---|---|---|---|---|---|---|---|---|---|---|
| HA | T | T | R | A | P | M | R | V | M | R | D | A | L | 0 |
| HB | S | S | R | A | P | M | R | V | M | R | D | A | L | 2 |
| HC | T | T | K | S | H | M | R | V | M | R | D | A | L | 3 |
| HD | T | T | R | A | P | I | R | V | M | R | D | A | L | 1 |
| HE | T | T | R | A | P | M | K | A | L | V | D | A | L | 4 |
| HF | T | T | R | A | P | M | R | V | M | R | D | V | L | 1 |
| HG | T | T | R | A | P | M | R | V | M | R | Q | A | L | 1 |

TABLE 2-continued

Heavy Chain Backmutations

| Ab | H28 | H30 | H38 | H40 | H41 | H48 | H66 | H67 | H69 | H71 | H72 | H93 | H108 | # back mutations |
|---|---|---|---|---|---|---|---|---|---|---|---|---|---|---|
| HH | T | T | R | A | P | M | R | V | M | R | D | A | P | 1 |
| HI | S | S | K | S | H | I | K | A | L | V | Q | V | P | 13 |

TABLE 3

Light Chain Backmutations

| Antibody | L21 | L22 | L36 | L37 | L45 | L63 | # back mutations |
|---|---|---|---|---|---|---|---|
| LA | I | S | F | Q | R | S | 0 |
| LB | L | F | F | Q | R | S | 2 |
| LC | I | S | L | F | R | S | 2 |
| LD | I | S | F | Q | K | S | 1 |
| LE | I | S | F | Q | R | T | 1 |
| LF | L | F | L | F | K | T | 6 |

Humanized antibodies were then expressed representing permutations of these chains of the humanized heavy and light chains. All of the heavy chains were expressed but only the HB heavy chain demonstrated appreciable binding (FIG. 2). The light chains all showed binding in combination with the HB heavy chain.

Based on the binding data from the first humanization round, a second humanization round was performed. Three positions, H73, H75, H78, in addition to H28, H30, H72, and H93 were identified in the heavy chain at which the human acceptor sequence differed from the donor sequence and that may affect antibody binding as a result of contacting antigen directly, affecting conformation of CDRs or affecting packing between heavy and light chains. One position, L4 in addition to L21, L22, L36, L37, L45, and L63 was identified in the light chain. 10 additional humanized heavy chains and one additional humanized light chain were made incorporating back mutations at different permutations of these positions. Backmutations are underlined and in bold. (Tables 4 and 5). The remainder of the positions are occupied by the residues from the human acceptor sequence.

TABLE 4

Heavy Chain Backmutations

| Antibody | H28 | H30 | H72 | H73 | H75 | H78 | H93 | # back mutations |
|---|---|---|---|---|---|---|---|---|
| HA | T | T | D | T | T | V | A | 0 |
| HB | S | S | D | T | T | V | A | 2 |
| HF | T | T | D | T | T | V | V | 1 |
| HG | T | T | Q | T | T | V | A | 1 |
| HK | T | T | D | K | S | A | A | 3 |
| HL | S | S | D | K | S | A | A | 5 |
| HM | S | S | Q | K | S | A | A | 6 |
| HN | S | S | Q | T | T | V | A | 3 |
| HO | S | S | Q | K | T | V | A | 4 |
| HQ | T | T | D | T | S | A | A | 2 |
| HR | S | S | D | T | S | A | A | 4 |
| HS | S | S | Q | T | S | A | A | 5 |
| HT | S | S | Q | T | T | V | V | 4 |
| HU | S | S | Q | K | S | A | V | 7 |

TABLE 5

Light Chain Backmutations

| Antibody | L4 | L21 | L22 | L36 | L37 | L45 | L63 | # back mutations |
|---|---|---|---|---|---|---|---|---|
| LA | M | I | S | F | Q | R | S | 0 |
| LB | M | L | F | F | Q | R | S | 2 |
| LC | M | I | S | L | F | R | S | 2 |
| LD | M | I | S | F | Q | K | S | 1 |
| LE | M | I | S | F | Q | R | T | 1 |
| LF | M | L | F | L | F | K | T | 6 |
| LG | L | I | S | L | F | R | S | 3 |

All of the heavy chains (except for HO and HK) were expressed. The binding curves are shown in FIGS. 4-7. The EC50's are summarized in the Table 6 below.

TABLE 6

EC$_{50}$s for select humanized anti-αvβ6 antibodies

| Ab | EC50 (nM) |
|---|---|
| HBLC | 8.14 |
| HLLC | 0.74 |
| HLLG | 0.97 |
| HMLC | 0.49 |
| HMLG | 1.07 |
| HNLC | 11.14 |
| HNLG | 3.16 |
| HRLC | 26.7 |
| HRLG | 23.9 |
| HSLC | 32.5 |
| HTLC | 3.7 |
| HULC | 0.93 |

Expression Data

Anti-B6 clones 437216 (R&D systems) was used for immunohistochemical analysis of various tumor types using formalin-fixed paraffin embedded tissues (FFPE).

Summary of the Expression Data for αvβ6 in Multitumor Array

| Tumor Origin | αvβ6+ expression (%) |
|---|---|
| Bladder | 65 |
| Head & Neck | 50 |
| Skin | 33 |
| Lung | 30 |
| Pancreas | 30 |
| Uterus | 30 |
| Breast | 26 |
| Colon | 20 |
| Prostate | 15 |
| Ovary | 14 |
| Stomach | 5 |

Anti-B6 clones 437216 (R&D systems) was used for immunohistochemical analysis of various tumor types using frozen tissue Summary of the Expression Data for αvβ6 in Frozen Tissue Samples

| Tumor Origin | αvβ6+ | # cases | % |
|---|---|---|---|
| Pancreatic | 10 | 9 | 100% |
| Head & Neck | 10 | 10 | 100% |

Anti-B6 clones 437216 (R&D systems) was also used for immunohistochemical analysis of various normal tissue types using formalin-fixed paraffin embedded tissues (FFPE) and frozen tissue. Normal breast, pancreas, esophagus, larynx, lung, skin, uterus, breast, colon, prostate, stomach, and ovary all had no B6 expression.

The 15H3 antibody was also used to stain frozen tumor and normal tissue samples. The normal tissue samples were negative for B6 expression. 23% (3/13) of triple negative breast cancer tissues showed mild to strong B6 expression. 100% of pancreatic cancer samples (5/5 samples) lung cancer samples (10/10) and gastric cancer samples (10/10) showed strong B6 expression.

In Vitro Anti-Tumor Activity of Murine 15H3 ADC

Anti-tumor activity of anti-αvβ6 ADCs in vitro was measured using cytotoxicity assays. A survey of αvβ6 expression in various cell lines by quantitative FACS analysis was performed. Referring to the table below, the murine 15H3 ADCs (the murine 15H3 antibody conjugated with vcMMAE or mcMMAF (both small molecules and/or linkers described in US20050238649)) were effective in killing αvβ6 cells.

| Cancer cell line | Copies/cell (×10³) | M15H3-vc-MMAE IC₅₀ (ng/ml) | M15H3-mc-MMAF IC₅₀ (ng/ml) |
|---|---|---|---|
| HupT4 | 184 | 35 | 16 |
| BxPC3 | 37 | 34 | 7 |
| HPAFII | 22 | 76 | >2000 |
| Panc08.13 | 137 | 93 | 1400 |
| Capan-1 | 19 | 365 | 1508 |
| SU8686 | 33 | No effect | No effect |
| 5637 | 36 | >1000 | >1000 |
| SW780 | 80 | 614 | 86 |
| RT4 | 42 | >1000 | >1000 |

Figure 9A:
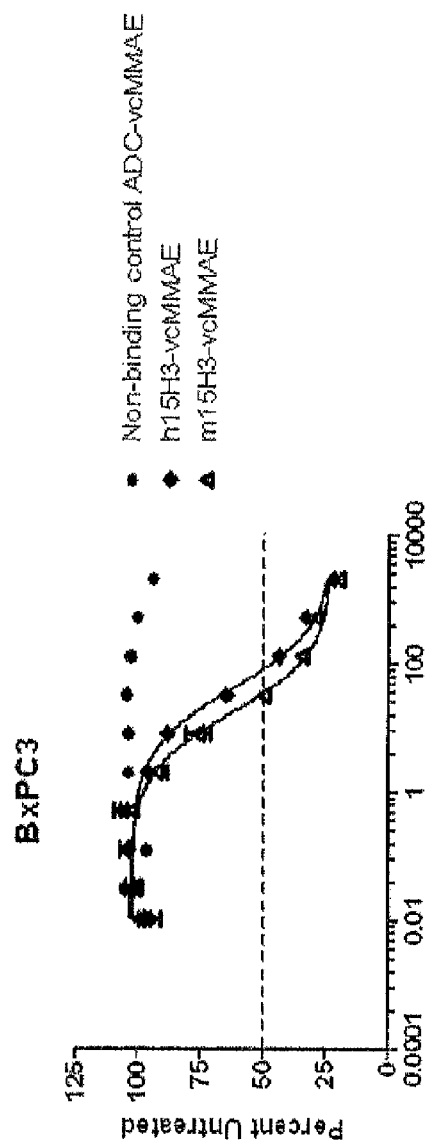
Figure 9B:
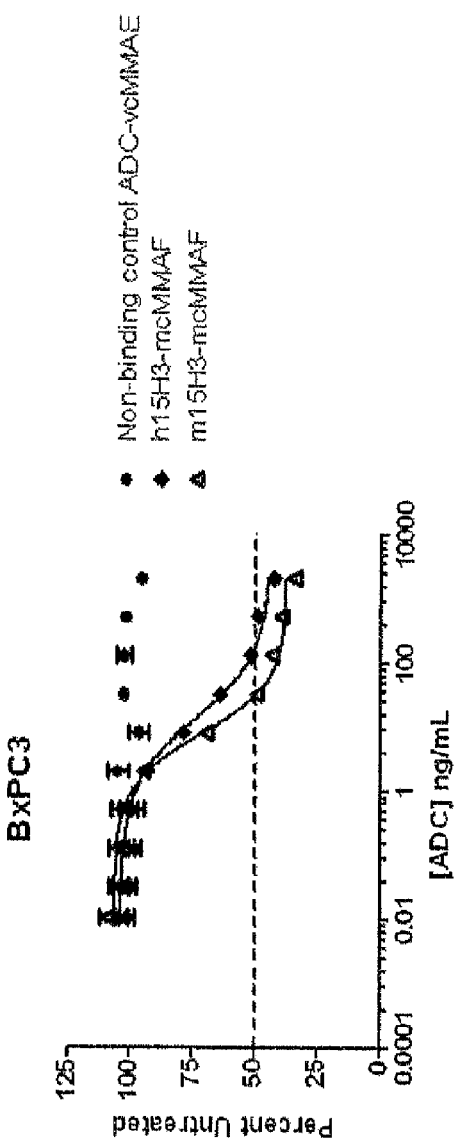

FIG. 9 shows that humanized 15H3 anti-αvβ6 ADCs behaved similarly as the mouse parental in cytotoxicity assays.

In Vivo Anti-Tumor Activity of Humanized Anti-αvβ6 ADCs

Figure 10:
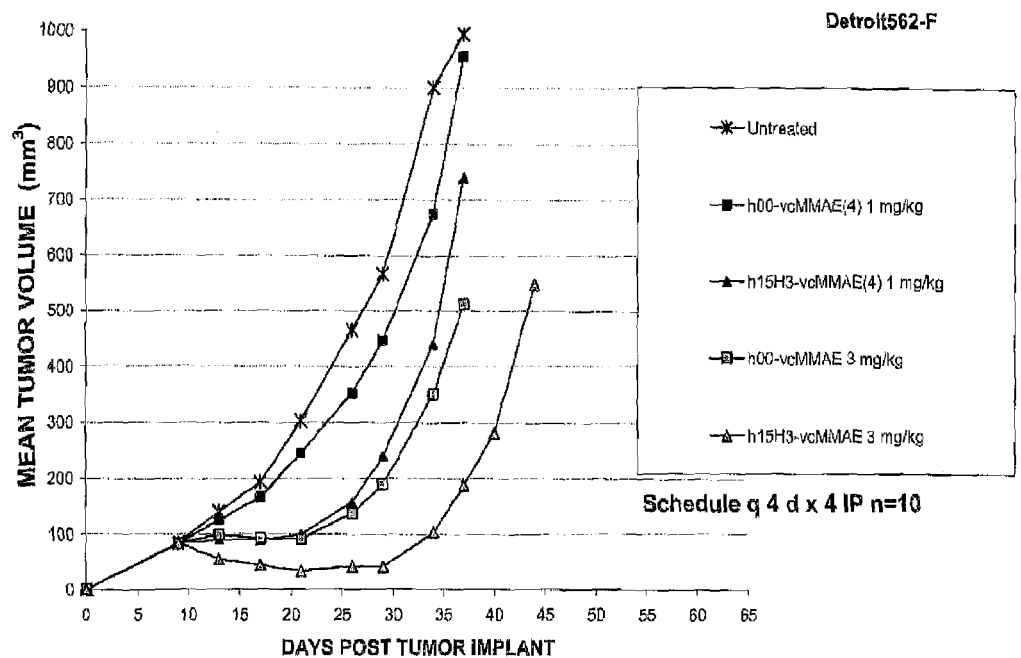
FIG. 10 shows the results of a xenograft study of the Detroit 562 head and neck cancer cell line in nude mice. The dose is indicated on the figure. The first administration was when the tumor reached approximately 100 mm$^3$.
Figure 11:
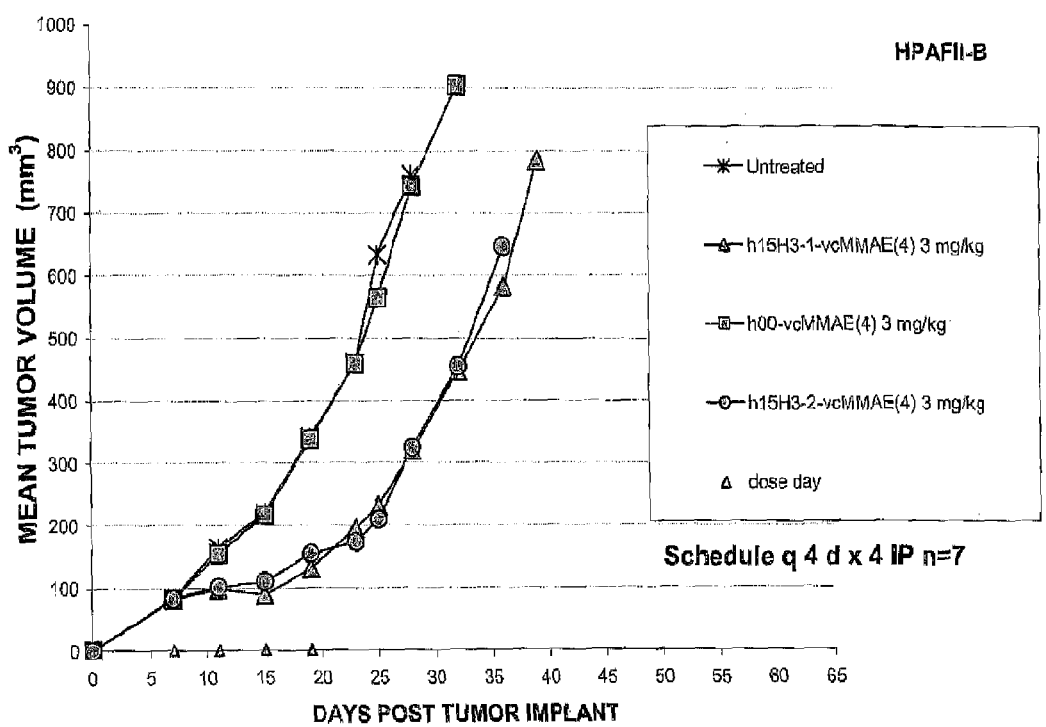
FIG. 11 shows the results of a xenograft study of the HPAFII pancreatic cancer cell line in nude mice. The dose and time of administration of indicated on the figure.
Figure 12:
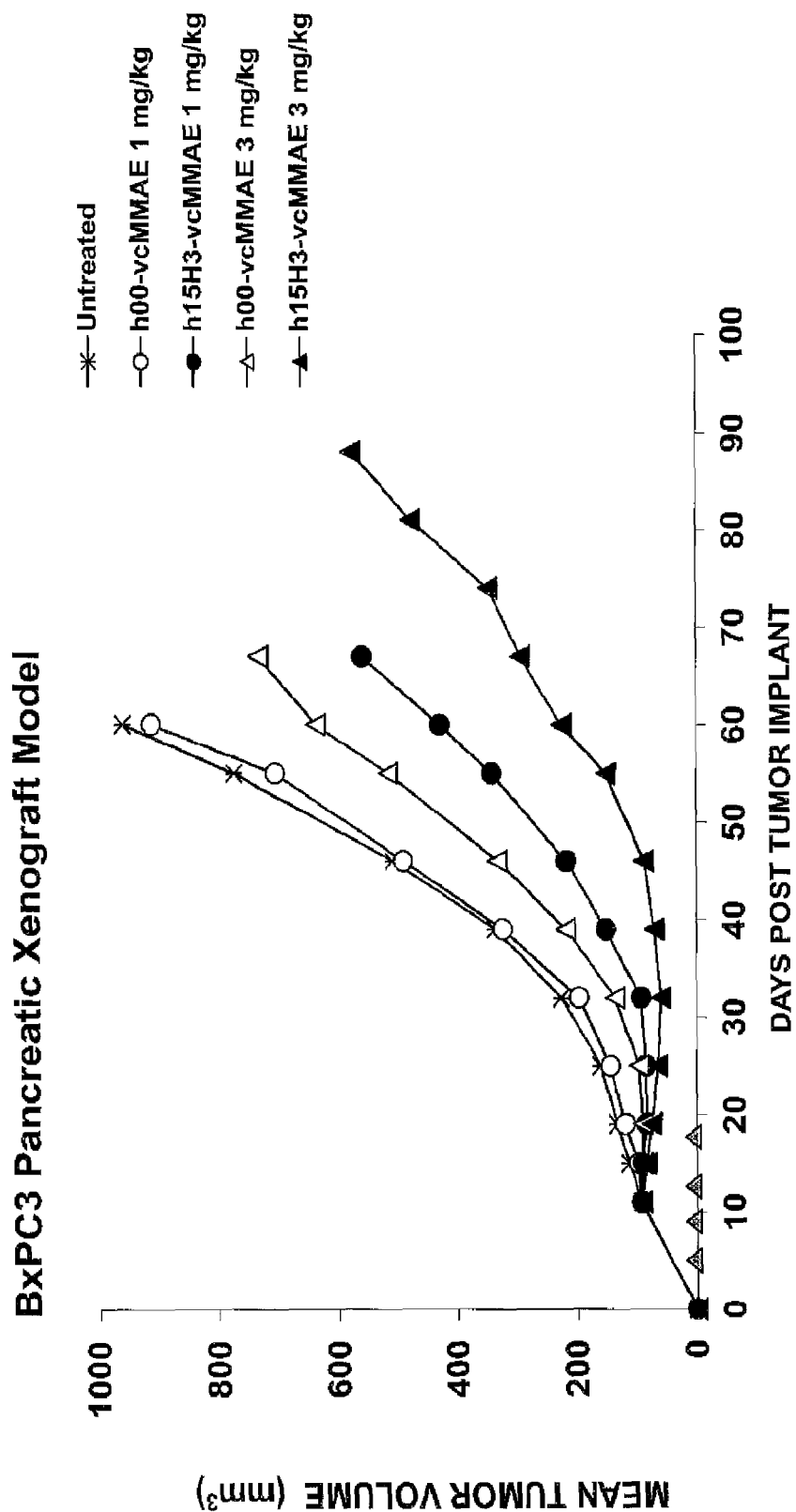
FIG. 12 shows the results of a xenograft study of the BxPC-3 pancreatic cancer cell line in nude mice. The dose and time of administration is indicated on the figure.

Using pancreatic cancer (HPAFII, BxPC-3) and head and neck cancer (Detroit 562) models, the anti-tumor activity of select humanized αvβ6 ADCs (average of 4 drugs per antibody) in vivo (FIGS. 10-12) was demonstrated. αvβ6 ADCs conjugated to vcMMAE showed significant tumor delay or tumor regression compared to untreated and control ADCs. h15H3-vcMMAE (4) refers to antibody drug conjugates of the humanized form of the parental murine antibody having an average of 4 vcMMAE drug linker molecules per antibody. h00-vcMMAE (4) refers to an antibody drug conjugate of a nonbinding control antibody having an average of 4 vcMMAE drug linker molecules per antibody. h15H3-1 is the HBLC construct, h15H3-2 is the HLLC construct and h15H3-3 is the HTLC construct.

Sequences

```
                                                                SEQ ID NO: 1
murine heavy chain variable region - protein
EVQLQQSGPELVKPGASVKISCKASGYSFSGYFMNWVKQSHGQSLEWIGLINPYNGDSFYNQKFKGKATLT

VQKSSSTAHMELQSLTSEDSAVFYCVRGLRRDFDYWGQGTPLTVSS
```

```
                                                                SEQ ID NO: 2
murine light chain variable region - protein
DVVLTQIPLTLSVTIGQPASLFCKSSQSLLDSDGKTYLNWLFQRPGQSPKRLIYLVSELDSGVPDRFTGSG

SGTDFTLKISRVEAEDLGVYYCWQGTHFPRTFGGGTKLEIKR
```

```
                                                                SEQ ID NO: 3
murine heavy chain CDR1 - protein
GYFMN
```

```
                                                                SEQ ID NO: 4
murine heavy chain CDR2 - protein
LINPYNGDSFYNQKFKG
```

```
                                                                SEQ ID NO: 5
murine heavy chain CDR3 - protein
GLRRDFDY
```

```
                                                                SEQ ID NO: 6
murine light chain CDR1 - protein
KSSQSLLDSDGKTYLN
```

```
                                                                SEQ ID NO: 7
murine light chain CDR2 - protein
LVSELDS
```

```
                                                                SEQ ID NO: 8
murine light chain CDR3 - protein
WQGTHFPRT
```

-continued

HA heavy chain variable region - protein  
SEQ ID NO: 9
QVQLVQSGAEVKKPGASVKVSCKASGYTFTGYFMNWVRQAPGQGLEWMGLINPYNGDSFY

NQKFKGRVTMTRDTSTSTVYMELSSLRSEDTAVYYCARGLRRDFDYWGQGTLVTVSS

LA light chain variable region - protein  
SEQ ID NO: 10
DVVMTQSPLSLPVTLGQPASISCKSSQSLLDSDGKTYLNWFQQRPGQSPRRLIYLVSELD

SGVPDRFSGSGSGTDFTLKISRVEAEDVGVYYCWQGTHFPRTFGGGTKLEIKR

HB heavy chain variable region - protein  
SEQ ID NO: 11
QVQLVQSGAEVKKPGASVKVSCKASGYSFSGYFMNWVRQAPGQGLEWMGLINPYNGDSFY

NQKFKGRVTMTRDTSTSTVYMELSSLRSEDTAVYYCARGLRRDFDYWGQGTLVTVSS

HF heavy chain variable region - protein  
SEQ ID NO: 12
QVQLVQSGAEVKKPGASVKVSCKASGYTFTGYFMNWVRQAPGQGLEWMGLINPYNGDSFY

NQKFKGRVTMTRDTSTSTVYMELSSLRSEDTAVYYCVRGLRRDFDYWGQGTLVTVSS

HG heavy chain variable region - protein  
SEQ ID NO: 13
QVQLVQSGAEVKKPGASVKVSCKASGYTFTGYFMNWVRQAPGQGLEWMGLINPYNGDSFY

NQKFKGRVTMTRQTSTSTVYMELSSLRSEDTAVYYCARGLRRDFDYWGQGTLVTVSS

HK heavy chain variable region - protein  
SEQ ID NO: 14
QVQLVQSGAEVKKPGASVKVSCKASGYTFTGYFMNWVRQAPGQGLEWMGLINPYNGDSFY

NQKFKGRVTMTRDKSSSTAYMELSSLRSEDTAVYYCARGLRRDFDYWGQGTLVTVSS

HL heavy chain variable region - protein  
SEQ ID NO: 15
QVQLVQSGAEVKKPGASVKVSCKASGYSFSGYFMNWVRQAPGQGLEWMGLINPYNGDSFY

NQKFKGRVTMTRDKSSSTAYMELSSLRSEDTAVYYCARGLRRDFDYWGQGTLVTVSS

HM heavy chain variable region - protein  
SEQ ID NO: 16
QVQLVQSGAEVKKPGASVKVSCKASGYSFSGYFMNWVRQAPGQGLEWMGLINPYNGDSFY

NQKFKGRVTMTRQKSSSTAYMELSSLRSEDTAVYYCARGLRRDFDYWGQGTLVTVSS

HN heavy chain variable region - protein  
SEQ ID NO: 17
QVQLVQSGAEVKKPGASVKVSCKASGYSFSGYFMNWVRQAPGQGLEWMGLINPYNGDSFY

NQKFKGRVTMTRQTSTSTVYMELSSLRSEDTAVYYCARGLRRDFDYWGQGTLVTVSS

HO heavy chain variable region - protein  
SEQ ID NO: 18
QVQLVQSGAEVKKPGASVKVSCKASGYSFSGYFMNWVRQAPGQGLEWMGLINPYNGDSFY

NQKFKGRVTMTRQKSTSTVYMELSSLRSEDTAVYYCARGLRRDFDYWGQGTLVTVSS

HQ heavy chain variable region - protein  
SEQ ID NO: 19
QVQLVQSGAEVKKPGASVKVSCKASGYTFTGYFMNWVRQAPGQGLEWMGLINPYNGDSFY

NQKFKGRVTMTRDTSSSTAYMELSSLRSEDTAVYYCARGLRRDFDYWGQGTLVTVSS

HR heavy chain variable region - protein  
SEQ ID NO: 20
QVQLVQSGAEVKKPGASVKVSCKASGYSFSGYFMNWVRQAPGQGLEWMGLINPYNGDSFY

NQKFKGRVTMTRDTSSSTAYMELSSLRSEDTAVYYCARGLRRDFDYWGQGTLVTVSS

HS heavy chain variable region - protein  
SEQ ID NO: 21
QVQLVQSGAEVKKPGASVKVSCKASGYSFSGYFMNWVRQAPGQGLEWMGLINPYNGDSFY

NQKFKGRVTMTRQTSSSTAYMELSSLRSEDTAVYYCARGLRRDFDYWGQGTLVTVSS

-continued

HT heavy chain variable region - protein  
SEQ ID NO: 22  
QVQLVQSGAEVKKPGASVKVSCKASGYSFSGYFMNWVRQAPGQGLEWMGLINPYNGDSFY

NQKFKGRVTMTRQTSTSTVYMELSSLRSEDTAVYYCVRGLRRDFDYWGQGTLVTVSS

HU heavy chain variable region - protein  
SEQ ID NO: 23  
QVQLVQSGAEVKKPGASVKVSCKASGYSFSGYFMNWVRQAPGQGLEWMGLINPYNGDSFY

NQKFKGRVTMTRQKSSSTAYMELSSLRSEDTAVYYCVRGLRRDFDYWGQGTLVTVSS

LB light chain variable region - protein  
SEQ ID NO: 24  
DVVMTQSPLSLPVTLGQPASLFCKSSQSLLDSDGKTYLNWFQQRPGQSPRRLIYLVSELD

SGVPDRFSGSGSGTDFTLKISRVEAEDVGVYYCWQGTHFPRTFGGGTKLEIKR

LC light chain variable region - protein  
SEQ ID NO: 25  
DVVMTQSPLSLPVTLGQPASISCKSSQSLLDSDGKTYLNWLFQRPGQSPRRLIYLVSELD

SGVPDRFSGSGSGTDFTLKISRVEAEDVGVYYCWQGTHFPRTFGGGTKLEIKR

LD light chain variable region - protein  
SEQ ID NO: 26  
DVVMTQSPLSLPVTLGQPASISCKSSQSLLDSDGKTYLNWFQQRPGQSPKRLIYLVSELD

SGVPDRFSGSGSGTDFTLKISRVEAEDVGVYYCWQGTHFPRTFGGGTKLEIKR

LE light chain variable region - protein  
SEQ ID NO: 27  
DVVMTQSPLSLPVTLGQPASISCKSSQSLLDSDGKTYLNWFQQRPGQSPRRLIYLVSELD

SGVPDRFTGSGSGTDFTLKISRVEAEDVGVYYCWQGTHFPRTFGGGTKLEIKR

LF light chain variable region - protein  
SEQ ID NO: 28  
DVVMTQSPLSLPVTLGQPASLFCKSSQSLLDSDGKTYLNWLFQRPGQSPKRLIYLVSELD

SGVPDRFTGSGSGTDFTLKISRVEAEDVGVYYCWQGTHFPRTFGGGTKLEIKR

LG light chain variable region - protein  
SEQ ID NO: 29  
DVVLTQSPLSLPVTLGQPASISCKSSQSLLDSDGKTYLNWLFQRPGQSPRRLIYLVSELD

SGVPDRFSGSGSGTDFTLKISRVEAEDVGVYYCWQGTHFPRTFGGGTKLEIKR human IgG1 heavy chain constant region - protein  
SEQ ID NO: 30  
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK human kappa light chain constant domain - protein  
SEQ ID NO: 31  
TVAAPSVFIFPPSDEQLKSGTASVVCLLNNFYPREAKVQWKVDNALQSGNSQESVTEQDS

KDSTYSLSSTLTLSKADYEKHKVYACEVTHQGLSSPVTKSFNRGEC human IgG1 heavy chain constant region S239C mutant - protein  
SEQ ID NO: 32  
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PCVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK

-continued murine heavy chain variable region signal peptide - protein
MGWSCIFLFLLSVTVGVFS

SEQ ID NO: 33 human heavy chain variable region signal peptide - protein
MAWVWTLLFLMAAAQSAQA

SEQ ID NO: 34 murine light chain variable region signal peptide - protein
MSPAQFLFLLVLWIRETNG

SEQ ID NO: 35 human light chain variable region signal peptide - protein
MKLPVRLLVLMFWIPASSS

SEQ ID NO: 36 mouse heavy chain variable region - nucleic acid
gaggttcagctgcagcagtctggacctgagttggtgaaacctggggcttcagtgaagatatcctgcaaggc ttctggttattcatttagtggctactttatgaactgggtgaaacagagccatggacagagccttgagtgga ttggacttattaatccttacaatggagactcttttttacaatcagaagttcaagggcaaggccacattgact gtacagaagtcctctagtacagcccacatggaactccagagcctgacatctgaagactctgcagtcttttta ttgtgttagagggttacgacgggactttgactattggggccaaggcaccctctcacagtctcctca

SEQ ID NO: 37 mouse light chain variable region - nucleic acid
Gatgttgtgttgacccagattccactcactttgtcggttaccattggacaaccagcctccctcttttgtaa gtcaagtcagagcctcttagatagtgatggaaagacatatttgaattggttatttcagaggccaggccagt ctccaaagcgccttatttatctggtgtctgaactggactctggagtccctgacaggttcactggcagtgga tcagggacagatttcacactgaaaatcagcagagtggaggctgaggatttgggagtttattattgctggca aggtacacattttcctcggacgttcggtggaggcaccaagctggaaatcaaacgg

SEQ ID NO: 38

HA heavy chain variable region - nucleic acid
Caggtgcagctggtgcagtctggagctgaggtgaagaagcctggagcctctgtgaaggtgtcctgtaaggc ctctggctacaccttcacaggctacttcatgaactgggtgaggcaggcccctggccagggcctggagtgga tgggcctgatcaaccccttacaatggagactccttctacaaccagaagttcaagggcagggtgaccatgacc agggacacctccacctccacagtgtacatggagctgtcctccctgaggtctgaggacacagctgtgtacta ctgtgccaggggcctgaggagggactttgactactggggccagggcaccctggtgacagtgtcctcc

SEQ ID NO: 39

HB heavy chain variable region - nucleic acid
Caggtgcagctggtgcagtctggagctgaggtgaagaagcctggagcctctgtgaaggtgtcctgtaaggc ctctggctacagcttctctggctacttcatgaactgggtgaggcaggcccctggccagggcctggagtgga tgggcctgatcaaccccttacaatggagactccttctacaaccagaagttcaagggcagggtgaccatgacc agggacacctccacctccacagtgtacatggagctgtcctccctgaggtctgaggacacagctgtgtacta ctgtgccaggggcctgaggagggactttgactactggggccagggcaccctggtgacagtgtcctcc

SEQ ID NO: 40

HL heavy chain variable region - nucleic acid
Caggtgcagctggtgcagtctggagctgaggtgaagaagcctggagcctctgtgaaggtgtcctgtaaggc ctctggctacagcttctctggctacttcatgaactgggtgaggcaggcccctggccagggcctggagtgga tgggcctgatcaaccccttacaatggagactccttctacaaccagaagttcaagggcagggtgaccatgacc agggacaagtcctcctccacagcttacatggagctgtcctccctgaggtctgaggacacagctgtgtacta ctgtgccaggggcctgaggagggactttgactactggggccagggcaccctggtgacagtgtcctcc

SEQ ID NO: 41

-continued

SEQ ID NO: 42

HT heavy chain variable region - nucleic acid
Caggtgcagctggtgcagtctggagctgaggtgaagaagcctggagcctctgtgaaggtgtcctgtaaggc ctctggctacagcttctctggctacttcatgaactgggtgaggcaggcccctggccagggcctggagtgga tgggcctgatcaaccccttacaatggagactccttctacaaccagaagttcaagggcagggtgaccatgacc aggcagacctccacctccacagtgtacatggagctgtcctccctgaggtctgaggacacagctgtgtacta ctgtgtcaggggcctgaggagggactttgactactggggccagggcaccctggtgacagtgtcctcc

SEQ ID NO: 43

HN heavy chain variable region - nucleic acid
Caggtgcagctggtgcagtctggagctgaggtgaagaagcctggagcctctgtgaaggtgtcctgtaaggc ctctggctacagcttctctggctacttcatgaactgggtgaggcaggcccctggccagggcctggagtgga tgggcctgatcaaccccttacaatggagactccttctacaaccagaagttcaagggcagggtgaccatgacc aggcagacctccacctccacagtgtacatggagctgtcctccctgaggtctgaggacacagctgtgtacta ctgtgccaggggcctgaggagggactttgactactggggccagggcaccctggtgacagtgtcctcc

SEQ ID NO: 44

HU heavy chain variable region - nucleic acid
Caggtgcagctggtgcagtctggagctgaggtgaagaagcctggagcctctgtgaaggtgtcctgtaaggc ctctggctacagcttctctggctacttcatgaactgggtgaggcaggcccctggccagggcctggagtgga tgggcctgatcaaccccttacaatggagactccttctacaaccagaagttcaagggcagggtgaccatgacc aggcagaagtcctcctccacagcttacatggagctgtcctccctgaggtctgaggacacagctgtgtacta ctgtgtcaggggcctgaggagggactttgactactggggccagggcaccctggtgacagtgtcctcc

SEQ ID NO: 45

LA light chain variable region - nucleic acid
gatgtggtgatgacccagtcccctctgtccctgcctgtgaccctgggccagcctgcctccatctcctgtaa gtcctcccagtccctgctggactctgatggcaagacctacctgaactggttccagcagaggcctggccagt cccctaggaggctgatctacctggtgtctgagctggactctggagtgcctgacaggttctctggctctggc tctggcacagacttcacccctgaagatctccagggtggaggctgaggatgtgggagtgtactactgttggca gggcacccacttccctaggacctttggaggtggaaccaagctggagatcaagcgt

SEQ ID NO: 46

LC light chain variable region - nucleic acid
gatgtggtgatgacccagtcccctctgtccctgcctgtgaccctgggccagcctgcctccatctcctgtaa gtcctcccagtccctgctggactctgatggcaagacctacctgaactggctgttccagaggcctggccagt cccctaggaggctgatctacctggtgtctgagctggactctggagtgcctgacaggttctctggctctggc tctggcacagacttcacccctgaagatctccagggtggaggctgaggatgtgggagtgtactactgttggca gggcacccacttccctaggacctttggaggtggaaccaagctggagatcaagcgt

SEQ ID NO: 47

LF light chain variable region - nucleic acid
Gatgtggtgatgacccagtcccctctgtccctgcctgtgaccctgggccagcctgcctccctgttctgtaa gtcctcccagtccctgctggactctgatggcaagacctacctgaactggctgttccagaggcctggccagt cccctaagaggctgatctacctggtgtctgagctggactctggagtgcctgacaggttcacaggctctggc tctggcacagacttcacccctgaagatctccagggtggaggctgaggatgtgggagtgtactactgttggca gggcacccacttccctaggacctttggaggtggaaccaagctggagatcaagcgt LG light chain variable region - nucleic acid  
SEQ ID NO: 48 gatgtggtgctgacccagtccctctgtccctgcctgtgaccctgggccagcctgcctccatctcctgtaa gtcctcccagtccctgctggactctgatggcaagacctacctgaactggctgttccagaggcctggccagt cccctaggaggctgatctacctggtgtctgagctggactctggagtgcctgacaggttctctggctctggc tctggcacagacttcaccctgaagatctccagggtggaggctgaggatgtgggagtgtactactgttggca gggcacccacttccctaggacctttggaggtggaaccaagctggagatcaagcgt murine heavy chain variable region signal peptide - nucleic acid  
SEQ ID NO: 49

Atgggatggagctgtatctttctctttctcctgtcagtaactgtaggtgtgttctct human heavy chain variable region signal peptide - nucleic acid  
SEQ ID NO: 50

Atggcttgggtgtggaccttgctattcctgatggcagctgcccaaagtgcccaagca murine light chain variable region signal peptide nucleic acid  
SEQ ID NO: 51 atgagtcctgcccagttcctgtttctgttagtgctctggattcgggaaaccaacggt human light chain variable region signal peptide - nucleic acid  
SEQ ID NO: 52

Atgaagttgcctgttaggctgttggtgctgatgttctggattcctgcttccagcagt human IgG1 heavy chain constant region - nucleic acid  
SEQ ID NO: 53 gctagcaccaagggcccatcggtcttccccctggcaccctcctccaagagcacctctgggggcacagcggccctgggctgcctggtcaaggactacttcc ccgaaccggtgacggtgtcgtggaactcaggcgccctgaccagcggcgtgcacaccttcccggctgtcctacagtcctcaggactctactccctcagcag cgtggtgaccgtgccctccagcagcttgggcacccagacctacatctgcaacgtgaatcacaagcccagcaacaccaaggtggacaagaaagttgagcc caaatcttgtgacaaaactcacacatgcccaccgtgcccagcacctgaactcctggggggaccgtcagtcttcctcttccccccaaaacccaaggacacc ctcatgatctcccggacccctgaggtcacatgcgtggtggtggacgtgagccacgaagaccctgaggtcaagttcaactggtacgtggacggcgtggagg tgcataatgccaagacaaagccgcgggaggagcagtacaacagcacgtaccgtgtggtcagcgtcctcaccgtcctgcaccaggactggctgaatggca aggagtacaagtgcaaggtctccaacaaagccctcccagcccccatcgagaaaaccatctccaaagccaaagggcagccccgagaaccacaggtgtac accctgcccccatcccgggatgagctgaccaagaaccaggtcagcctgacctgcctggtcaaaggcttctatcccagcgacatcgccgtggagtgggag agcaatgggcagccggagaacaactacaagaccacgcctcccgtgctggactccgacggctccttcacctctacagcaagctcaccgtggacaagagc aggtggcagcaggggaacgtcttctcatgctccgtgatgcatgaggctctgcacaaccactacacgcagaagagcctctccctgtctccgggtaaa human kappa light chain constant domain - nucleic acid  
SEQ ID NO: 54

Actgtggcggcgccatctgtcttcatcttcccgccatctgatgagcagttgaaatctggaactgcctctgttgtgtgcctgctgaataacttctatccca gagaggccaaagtacagtggaaggtggataacgccctccaatcgggtaactcccaggagagtgtcacagagcaggacagcaaggacagcacctacagcct cagcagcaccctgacgctgagcaaagcagactacgagaaacacaaagtctacgcctgcgaagtcacccatcagggcctgagctcgcccgtcacaaagagc ttcaacaggggagagtgt human IgG1 heavy chain constant region S239C mutant - nucleic acid  
SEQ ID NO: 55

Gctagcaccaagggcccatctgtcacccctggcaccctcctccaagagcacctctgggggcacagctgccctgggctgcctggtcaaggactacttcc ctgaacctgtgacagtgtcctggaactcaggcgccctgaccagcggcgtgcacaccaccggctgtcctacagtcctcaggactctactccctcagcagc gtggtgaccgtgccctccagcagcttgggcacccagacctacatctgcaacgtgaatcacaagcccagcaacaccaaggtggacaagaaagttgagccc aaatcttgtgacaaaactcacacatgcccaccgtgcccagcacctgaactcctggggggaccgtgtgtcttcctcttccccccaaaacccaaggacaccc tcatgatctcccggacccctgaggtcacatgcgtggtggtggacgtgagccacgaagaccctgaggtcaagttcaactggtacgtggacggcgtggaggt gcataatgccaagacaaagccgcgggaggagcagtacaacagcacgtaccgtgtggtcagcgtcctcaccgtcctgcaccaggactggctgaatggcaa ggagtacaagtgcaaggtctccaacaaagccctcccagcccccatcgagaaaaccatctccaaagccaaagggcagccccgagaaccacaggtgtaca ccctgcccccatcccgggatgagctgaccaagaaccaggtcagcctgacctgcctggtcaaaggcttctatcccagcgacatcgccgtggagtgggaga gcaatgggcagccggagaacaactacaagaccacgcctcccgtgctggactccgacggctccacttcctctacagcaagctcaccgtggacaagagca ggtggcagcaggggaacgtcttctcatgctccgtgatgcatgaggctctgcacaaccactacacacagaagagcctctccctgtctccgggtaaa

What is claimed is:

1. An isolated murine 15H3 monoclonal antibody that specifically binds integrin αvβ6 wherein the antibody comprises a heavy chain variable region comprising the sequence set forth in SEQ ID NO:1 and a light chain variable region comprising the sequence set forth in SEQ ID NO:2; and chimeric or humanized forms thereof.

2. An isolated monoclonal antibody that specifically binds integrin αvβ6 comprising heavy chain complementary determining region (CDR) sequences as set forth in SEQ ID NO:3 (CDR1), SEQ ID NO:4 (CDR2), and SEQ ID NO:5 (CDR3), and light chain CDR sequences as set forth in SEQ ID NO:6 (CDR4), SEQ ID NO:7 (CDR5), and SEQ ID NO:8 (CDR6).

3. A humanized antibody that specifically binds integrin αvβ6 having the heavy chain variable region having the amino acid sequence set forth in HB (SEQ ID NO:11) and a light chain variable region having the amino acid sequence set forth in LA (SEQ ID NO:10), LB (SEQ ID NO:24), LC (SEQ ID NO:25), LD (SEQ ID NO:26), LE (SEQ ID NO:27), LF (SEQ ID NO:28) or LG (SEQ ID NO:29); having the heavy chain variable region having the amino acid sequence set forth in HT (SEQ ID NO:22) and a light chain variable region having the amino acid sequence set forth in LA (SEQ ID NO:10), LB (SEQ ID NO:24), LC (SEQ ID NO:25), LD (SEQ ID NO:26), LE (SEQ ID NO:27), LF (SEQ ID NO:28) or LG (SEQ ID NO:29); having the heavy chain variable region having the amino acid sequence set forth in HL (SEQ ID NO:15) and a light chain variable region having the amino acid sequence set forth in LA (SEQ ID NO:10), LB (SEQ ID NO:24), LC (SEQ ID NO:25), LD (SEQ ID NO:26), LE (SEQ ID NO:27), LF (SEQ ID NO:28) or LG (SEQ ID NO:29); having the heavy chain variable region having the amino acid sequence set forth in HU (SEQ ID NO:23) and a light chain variable region having the amino acid sequence set forth in LA (SEQ ID NO:10), LB (SEQ ID NO:24), LC (SEQ ID NO:25), LD (SEQ ID NO:26), LE (SEQ ID NO:27), LF (SEQ ID NO:28) or LG (SEQ ID NO:29); having the heavy chain variable region having the amino acid sequence set forth in HN (SEQ ID NO:17) and a light chain variable region having the amino acid sequence set forth in LA (SEQ ID NO:10), LB (SEQ ID NO:24), LC (SEQ ID NO:25), LD (SEQ ID NO:26), LE (SEQ ID NO:27), LF (SEQ ID NO:28) or LG (SEQ ID NO:29) or having the heavy chain variable region having the amino acid sequence set forth in HM (SEQ ID NO:16) and a light chain variable region having the amino acid sequence set forth in LA (SEQ ID NO:10), LB (SEQ ID NO:24), LC (SEQ ID NO:25), LD (SEQ ID NO:26), LE (SEQ ID NO:27), LF (SEQ ID NO:28) or LG (SEQ ID NO:29).

4. The antibody of claim 1 wherein the antibody is an antigen binding fragment.

5. The antibody of claim 1, wherein the heavy chain variable region is fused to a human heavy chain constant region and the light chain variable region is fused to a human light chain constant region.

6. The antibody of claim 5, wherein the heavy chain constant region is a mutant form of natural human constant region which has reduced binding to an Fcgamma receptor relative to the natural human constant region.

7. The antibody of claim 5, wherein the heavy chain constant region is of IgG1 isotype.

8. The antibody of claim 1, wherein the antibody is conjugated to a cytotoxic agent.

9. The antibody of claim 1, wherein the antibody is a chimeric form of the murine 15H3 antibody and comprises the heavy chain variable region comprising the sequence set forth in SEQ ID NO:1 fused to a human heavy chain constant region, and the light chain variable region comprising the sequence set forth in SEQ ID NO:2 fused to a human light chain constant region.

10. The antibody of claim 1 that is purified.

11. A pharmaceutical composition an antibody of claim 1 wherein comprising the antibody is a chimeric or humanized antibody.

12. An isolated nucleic acid encoding a heavy chain variable region and a light chain variable region as defined in claim 1.

13. A method of treating a patient having pancreatic cancer or head and neck cancer, comprising administering to the patient an effective regime of an antibody of claim 8 wherein the antibody is a chimeric, human, or humanized antibody.

\* \* \* \* \*

UNITED STATES PATENT AND TRADEMARK OFFICE
CERTIFICATE OF CORRECTION

PATENT NO. : 9,493,566 B2  
APPLICATION NO. : 14/378746  
DATED : November 15, 2016  
INVENTOR(S) : Maureen Ryan et al.

Page 1 of 1

It is certified that error appears in the above-identified patent and that said Letters Patent is hereby corrected as shown below:

On the Title Page

Item (72), replace "Sussman Django" with --Django Sussman--

Signed and Sealed this  
Tenth Day of January, 2017

Michelle K. Lee  
*Director of the United States Patent and Trademark Office*

SEQUENCE LISTING

<160> NUMBER OF SEQ ID NOS: 55

<210> SEQ ID NO 1
<211> LENGTH: 117
<212> TYPE: PRT
<213> ORGANISM: Artificial
<220> FEATURE:
<223> OTHER INFORMATION: murine heavy chain variable region

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Gly Tyr
                20                  25                  30

Phe Met Asn Trp Val Lys Gln Ser His Gly Gln Ser Leu Glu Trp Ile
            35                  40                  45

Gly Leu Ile Asn Pro Tyr Asn Gly Asp Ser Phe Tyr Asn Gln Lys Phe
        50                  55                  60

Lys Gly Lys Ala Thr Leu Thr Val Gln Lys Ser Ser Ser Thr Ala His
65                  70                  75                  80

Met Glu Leu Gln Ser Leu Thr Ser Glu Asp Ser Ala Val Phe Tyr Cys
                85                  90                  95

Val Arg Gly Leu Arg Arg Asp Phe Asp Tyr Trp Gly Gln Gly Thr Pro
                100                 105                 110

Leu Thr Val Ser Ser
            115

<210> SEQ ID NO 2
<211> LENGTH: 113
<212> TYPE: PRT
<213> ORGANISM: Artificial
<220> FEATURE:
<223> OTHER INFORMATION: murine light chain variable region

<400> SEQUENCE: 2

Asp Val Val Leu Thr Gln Ile Pro Leu Thr Leu Ser Val Thr Ile Gly
1               5                   10                  15

Gln Pro Ala Ser Leu Phe Cys Lys Ser Ser Gln Ser Leu Leu Asp Ser
                20                  25                  30

Asp Gly Lys Thr Tyr Leu Asn Trp Leu Phe Gln Arg Pro Gly Gln Ser
            35                  40                  45

Pro Lys Arg Leu Ile Tyr Leu Val Ser Glu Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
                100                 105                 110

Arg

<210> SEQ ID NO 3
<211> LENGTH: 5
<212> TYPE: PRT
<213> ORGANISM: Artificial
<220> FEATURE:
<223> OTHER INFORMATION: murine heavy chain CDR1

```
<400> SEQUENCE: 3

Gly Tyr Phe Met Asn
1               5

<210> SEQ ID NO 4
<211> LENGTH: 17
<212> TYPE: PRT
<213> ORGANISM: Artificial
<220> FEATURE:
<223> OTHER INFORMATION: murine heavy chain CDR2

<400> SEQUENCE: 4

Leu Ile Asn Pro Tyr Asn Gly Asp Ser Phe Tyr Asn Gln Lys Phe Lys
1               5                   10                  15

Gly

<210> SEQ ID NO 5
<211> LENGTH: 8
<212> TYPE: PRT
<213> ORGANISM: Artificial
<220> FEATURE:
<223> OTHER INFORMATION: murine heavy chain CDR3

<400> SEQUENCE: 5

Gly Leu Arg Arg Asp Phe Asp Tyr
1               5

<210> SEQ ID NO 6
<211> LENGTH: 16
<212> TYPE: PRT
<213> ORGANISM: Artificial
<220> FEATURE:
<223> OTHER INFORMATION: murine light chain CDR1

<400> SEQUENCE: 6

Lys Ser Ser Gln Ser Leu Leu Asp Ser Asp Gly Lys Thr Tyr Leu Asn
1               5                   10                  15

<210> SEQ ID NO 7
<211> LENGTH: 7
<212> TYPE: PRT
<213> ORGANISM: Artificial
<220> FEATURE:
<223> OTHER INFORMATION: murine light chain CDR2

<400> SEQUENCE: 7

Leu Val Ser Glu Leu Asp Ser
1               5

<210> SEQ ID NO 8
<211> LENGTH: 9
<212> TYPE: PRT
<213> ORGANISM: Artificial
<220> FEATURE:
<223> OTHER INFORMATION: murine light chain CDR3

<400> SEQUENCE: 8

Trp Gln Gly Thr His Phe Pro Arg Thr
1               5

<210> SEQ ID NO 9
<211> LENGTH: 117
<212> TYPE: PRT
<213> ORGANISM: Artificial
<220> FEATURE:
<223> OTHER INFORMATION: HA heavy chain variable region
```

-continued

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Arg Arg Asp Phe Asp Tyr Trp Gly Gln Gly Thr Leu
            100                 105                 110

Val Thr Val Ser Ser
        115

<210> SEQ ID NO 10
<211> LENGTH: 113
<212> TYPE: PRT
<213> ORGANISM: Artificial
<220> FEATURE:
<223> OTHER INFORMATION: LA light chain variable region

<400> SEQUENCE: 10

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

Arg

<210> SEQ ID NO 11
<211> LENGTH: 117
<212> TYPE: PRT
<213> ORGANISM: Artificial
<220> FEATURE:
<223> OTHER INFORMATION: HB heavy chain variable region

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Phe Met Asn Trp Val Arg Gln Ala Pro Gly Gln Gly Leu Glu Trp Met
        35                  40                  45

```
Gly Leu Ile Asn Pro Tyr Asn Gly Asp Ser Phe Tyr Asn Gln Lys Phe
        50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Leu Arg Arg Asp Phe Asp Tyr Trp Gly Gln Gly Thr Leu
            100                 105                 110

Val Thr Val Ser Ser
            115

<210> SEQ ID NO 12
<211> LENGTH: 117
<212> TYPE: PRT
<213> ORGANISM: Artificial
<220> FEATURE:
<223> OTHER INFORMATION: HF heavy chain variable region

<400> SEQUENCE: 12

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Phe Met Asn Trp Val Arg Gln Ala Pro Gly Gln Gly Leu Glu Trp Met
             35                  40                  45

Gly Leu Ile Asn Pro Tyr Asn Gly Asp Ser Phe Tyr Asn Gln Lys Phe
        50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Val Arg Gly Leu Arg Arg Asp Phe Asp Tyr Trp Gly Gln Gly Thr Leu
            100                 105                 110

Val Thr Val Ser Ser
            115

<210> SEQ ID NO 13
<211> LENGTH: 117
<212> TYPE: PRT
<213> ORGANISM: Artificial
<220> FEATURE:
<223> OTHER INFORMATION: HG heavy chain variable region

<400> SEQUENCE: 13

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Phe Met Asn Trp Val Arg Gln Ala Pro Gly Gln Gly Leu Glu Trp Met
             35                  40                  45

Gly Leu Ile Asn Pro Tyr Asn Gly Asp Ser Phe Tyr Asn Gln Lys Phe
        50                  55                  60

Lys Gly Arg Val Thr Met Thr Arg Gln Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95
```

```
Ala Arg Gly Leu Arg Arg Asp Phe Asp Tyr Trp Gln Gly Thr Leu
            100                 105                 110

Val Thr Val Ser Ser
            115

<210> SEQ ID NO 14
<211> LENGTH: 117
<212> TYPE: PRT
<213> ORGANISM: Artificial
<220> FEATURE:
<223> OTHER INFORMATION: HK heavy chain variable region

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
    50                  55                  60

Lys Gly Arg Val Thr Met Thr Arg Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Arg Arg Asp Phe Asp Tyr Trp Gln Gly Thr Leu
            100                 105                 110

Val Thr Val Ser Ser
            115

<210> SEQ ID NO 15
<211> LENGTH: 117
<212> TYPE: PRT
<213> ORGANISM: Artificial
<220> FEATURE:
<223> OTHER INFORMATION: HL heavy chain variable region

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
    50                  55                  60

Lys Gly Arg Val Thr Met Thr Arg Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Arg Arg Asp Phe Asp Tyr Trp Gln Gly Thr Leu
            100                 105                 110

Val Thr Val Ser Ser
            115

<210> SEQ ID NO 16
<211> LENGTH: 117
<212> TYPE: PRT
<213> ORGANISM: Artificial
```

```
<220> FEATURE:
<223> OTHER INFORMATION: HM heavy chain variable region

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
    50                  55                  60

Lys Gly Arg Val Thr Met Thr Arg Gln Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Arg Arg Asp Phe Asp Tyr Trp Gly Gln Gly Thr Leu
            100                 105                 110

Val Thr Val Ser Ser
        115

<210> SEQ ID NO 17
<211> LENGTH: 117
<212> TYPE: PRT
<213> ORGANISM: Artificial
<220> FEATURE:
<223> OTHER INFORMATION: HN heavy chain variable region

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
    50                  55                  60

Lys Gly Arg Val Thr Met Thr Arg Gln Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Leu Arg Arg Asp Phe Asp Tyr Trp Gly Gln Gly Thr Leu
            100                 105                 110

Val Thr Val Ser Ser
        115

<210> SEQ ID NO 18
<211> LENGTH: 117
<212> TYPE: PRT
<213> ORGANISM: Artificial
<220> FEATURE:
<223> OTHER INFORMATION: HO heavy chain variable region

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30
```

```
Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
 50                  55                  60

Lys Gly Arg Val Thr Met Thr Arg Gln Lys Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Leu Arg Arg Asp Phe Asp Tyr Trp Gly Gln Gly Thr Leu
            100                 105                 110

Val Thr Val Ser Ser
            115

<210> SEQ ID NO 19
<211> LENGTH: 117
<212> TYPE: PRT
<213> ORGANISM: Artificial
<220> FEATURE:
<223> OTHER INFORMATION: HQ heavy chain variable region

<400> SEQUENCE: 19

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Phe Met Asn Trp Val Arg Gln Ala Pro Gly Gln Gly Leu Glu Trp Met
            35                  40                  45

Gly Leu Ile Asn Pro Tyr Asn Gly Asp Ser Phe Tyr Asn Gln Lys Phe
 50                  55                  60

Lys Gly Arg Val Thr Met Thr Arg Asp Thr Ser Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Arg Arg Asp Phe Asp Tyr Trp Gly Gln Gly Thr Leu
            100                 105                 110

Val Thr Val Ser Ser
            115

<210> SEQ ID NO 20
<211> LENGTH: 117
<212> TYPE: PRT
<213> ORGANISM: Artificial
<220> FEATURE:
<223> OTHER INFORMATION: HR heavy chain variable region

<400> SEQUENCE: 20

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Ser Gly Tyr
                 20                  25                  30

Phe Met Asn Trp Val Arg Gln Ala Pro Gly Gln Gly Leu Glu Trp Met
            35                  40                  45

Gly Leu Ile Asn Pro Tyr Asn Gly Asp Ser Phe Tyr Asn Gln Lys Phe
 50                  55                  60

Lys Gly Arg Val Thr Met Thr Arg Asp Thr Ser Ser Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Gly Leu Arg Arg Asp Phe Asp Tyr Trp Gln Gly Thr Leu
            100                 105                 110

Val Thr Val Ser Ser
        115

<210> SEQ ID NO 21
<211> LENGTH: 117
<212> TYPE: PRT
<213> ORGANISM: Artificial
<220> FEATURE:
<223> OTHER INFORMATION: HS heavy chain variable region

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
    50                  55                  60

Lys Gly Arg Val Thr Met Thr Arg Gln Thr Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Arg Arg Asp Phe Asp Tyr Trp Gln Gly Thr Leu
            100                 105                 110

Val Thr Val Ser Ser
        115

<210> SEQ ID NO 22
<211> LENGTH: 117
<212> TYPE: PRT
<213> ORGANISM: Artificial
<220> FEATURE:
<223> OTHER INFORMATION: HT heavy chain variable region

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
            20                  25                  30

Phe Met Asn Trp Val Arg Gln Ala Pro Gly Gln Gly Leu Glu Trp Met
        35                  40                  45

Gly Leu Ile Asn Pro Tyr Asn Gly Asp Ser Phe Tyr Asn Gln Lys Phe
    50                  55                  60

Lys Gly Arg Val Thr Met Thr Arg Gln Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Val Arg Gly Leu Arg Arg Asp Phe Asp Tyr Trp Gln Gly Thr Leu
            100                 105                 110

Val Thr Val Ser Ser
        115

<210> SEQ ID NO 23
<211> LENGTH: 117
<212> TYPE: PRT
<213> ORGANISM: Artificial

```
<220> FEATURE:
<223> OTHER INFORMATION: HU heavy chain variable region

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Ser Gly Tyr
                20                  25                  30

Phe Met Asn Trp Val Arg Gln Ala Pro Gly Gln Gly Leu Glu Trp Met
            35                  40                  45

Gly Leu Ile Asn Pro Tyr Asn Gly Asp Ser Tyr Tyr Asn Gln Lys Phe
        50                  55                  60

Lys Gly Arg Val Thr Met Thr Arg Gln Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Val Arg Gly Leu Arg Arg Asp Phe Asp Tyr Trp Gly Gln Gly Thr Leu
                100                 105                 110

Val Thr Val Ser Ser
            115

<210> SEQ ID NO 24
<211> LENGTH: 113
<212> TYPE: PRT
<213> ORGANISM: Artificial
<220> FEATURE:
<223> OTHER INFORMATION: LB light chain variable region

<400> SEQUENCE: 24

Asp Val Val Met Thr Gln Ser Pro Leu Ser Leu Pro Val Thr Leu Gly
1               5                   10                  15

Gln Pro Ala Ser Leu Phe Cys Lys Ser Ser Gln Ser Leu Leu Asp Ser
                20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Glu Leu Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Leu Glu Ile Lys
                100                 105                 110

Arg

<210> SEQ ID NO 25
<211> LENGTH: 113
<212> TYPE: PRT
<213> ORGANISM: Artificial
<220> FEATURE:
<223> OTHER INFORMATION: LC light chain variable region

<400> SEQUENCE: 25

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
                20                  25                  30
```

Asp Gly Lys Thr Tyr Leu Asn Trp Leu Phe Gln Pro Gly Gln Ser
                35                  40                  45

Pro Arg Arg Leu Ile Tyr Leu Val Ser Glu Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gly Gly Thr Lys Leu Glu Ile Lys
                100                 105                 110

Arg

<210> SEQ ID NO 26
<211> LENGTH: 113
<212> TYPE: PRT
<213> ORGANISM: Artificial
<220> FEATURE:
<223> OTHER INFORMATION: LD light chain variable region

<400> SEQUENCE: 26

Asp Val Val Met Thr Gln Ser Pro Leu Ser Leu Pro Val Thr Leu Gly
 1                5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Phe Gln Gln Arg Pro Gly Gln Ser
                35                  40                  45

Pro Lys Arg Leu Ile Tyr Leu Val Ser Glu Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gly Gly Thr Lys Leu Glu Ile Lys
                100                 105                 110

Arg

<210> SEQ ID NO 27
<211> LENGTH: 113
<212> TYPE: PRT
<213> ORGANISM: Artificial
<220> FEATURE:
<223> OTHER INFORMATION: LE light chain variable region

<400> SEQUENCE: 27

Asp Val Val Met Thr Gln Ser Pro Leu Ser Leu Pro Val Thr Leu Gly
 1                5                  10                  15

Gln Pro Ala Ser Ile Ser Cys Lys Ser Ser Gln Ser Leu Leu Asp Ser
                 20                  25                  30

Asp Gly Lys Thr Tyr Leu Asn Trp Phe Gln Gln Arg Pro Gly Gln Ser
                35                  40                  45

Pro Arg Arg Leu Ile Tyr Leu Val Ser Glu Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

```
Thr His Phe Pro Arg Thr Phe Gly Gly Gly Thr Lys Leu Glu Ile Lys
            100                 105                 110
Arg

<210> SEQ ID NO 28
<211> LENGTH: 113
<212> TYPE: PRT
<213> ORGANISM: Artificial
<220> FEATURE:
<223> OTHER INFORMATION: LF light chain variable region

<400> SEQUENCE: 28

Asp Val Val Met Thr Gln Ser Pro Leu Ser Leu Pro Val Thr Leu Gly
1               5                   10                  15

Gln Pro Ala Ser Leu Phe Cys Lys Ser Ser Gln Ser Leu Leu Asp Ser
            20                  25                  30

Asp Gly Lys Thr Tyr Leu Asn Trp Leu Phe Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110
Arg

<210> SEQ ID NO 29
<211> LENGTH: 113
<212> TYPE: PRT
<213> ORGANISM: Artificial
<220> FEATURE:
<223> OTHER INFORMATION: LG light chain variable region

<400> SEQUENCE: 29

Asp Val Val Leu Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Phe Gln Arg Pro Gly Gln Ser
        35                  40                  45

Pro Arg Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110
Arg

<210> SEQ ID NO 30
<211> LENGTH: 330
<212> TYPE: PRT
<213> ORGANISM: Artificial
<220> FEATURE:
<223> OTHER INFORMATION: human IgG1 heavy chain constant region
```

<400> SEQUENCE: 30

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 31
<211> LENGTH: 106
<212> TYPE: PRT
<213> ORGANISM: Artificial
<220> FEATURE:
<223> OTHER INFORMATION: human kappa light chain constant domain

<400> SEQUENCE: 31

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 32
<211> LENGTH: 330
<212> TYPE: PRT
<213> ORGANISM: Artificial
<220> FEATURE:
<223> OTHER INFORMATION: human IgG1 heavy chain constant region S239C
      mutant

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

-continued

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 19
<212> TYPE: PRT
<213> ORGANISM: Artificial
<220> FEATURE:
<223> OTHER INFORMATION: murine heavy chain variable region signal
      peptide

<400> SEQUENCE: 33

Met Gly Trp Ser Cys Ile Phe Leu Phe Leu Leu Ser Val Thr Val Gly
1               5                   10                  15

Val Phe Ser

<210> SEQ ID NO 34
<211> LENGTH: 19
<212> TYPE: PRT
<213> ORGANISM: Artificial
<220> FEATURE:
<223> OTHER INFORMATION: human heavy chain variable region signal
      peptide

<400> SEQUENCE: 34

Met Ala Trp Val Trp Thr Leu Leu Phe Leu Met Ala Ala Ala Gln Ser
1               5                   10                  15

Ala Gln Ala

<210> SEQ ID NO 35
<211> LENGTH: 19
<212> TYPE: PRT
<213> ORGANISM: Artificial
<220> FEATURE:
<223> OTHER INFORMATION: murine light chain variable region signal
      peptide

<400> SEQUENCE: 35

Met Ser Pro Ala Gln Phe Leu Phe Leu Leu Val Leu Trp Ile Arg Glu
1               5                   10                  15

Thr Asn Gly

<210> SEQ ID NO 36
<211> LENGTH: 19
<212> TYPE: PRT
<213> ORGANISM: Artificial
<220> FEATURE:
<223> OTHER INFORMATION: human light chain variable region signal
      peptide

<400> SEQUENCE: 36

Met Lys Leu Pro Val Arg Leu Leu Val Leu Met Phe Trp Ile Pro Ala
1               5                   10                  15

Ser Ser Ser

<210> SEQ ID NO 37
<211> LENGTH: 351
<212> TYPE: DNA
<213> ORGANISM: Artificial
<220> FEATURE:
<223> OTHER INFORMATION: mouse heavy chain variable region

<400> SEQUENCE: 37
gaggttcagc tgcagcagtc tggacctgag ttggtgaaac ctggggcttc agtgaagata     60
tcctgcaagg cttctggtta ttcatttagt ggctacttta tgaactgggt gaaacagagc    120
catggacaga gccttgagtg gattggactt attaatcctt acaatggaga ctcttttac     180 aatcagaagt tcaagggcaa ggccacattg actgtacaga gtcctctag tacagcccac     240 atggaactcc agagcctgac atctgaagac tctgcagtct tttattgtgt tagagggtta    300
cgacgggact tgactattg gggccaaggc accctctca cagtctcctc a               351

<210> SEQ ID NO 38
<211> LENGTH: 339
<212> TYPE: DNA
<213> ORGANISM: Artificial
<220> FEATURE:
<223> OTHER INFORMATION: mouse light chain variable region

<400> SEQUENCE: 38
gatgttgtgt tgacccagat tccactcact ttgtcggtta ccattggaca accagcctcc     60
ctcttttgta agtcaagtca gagcctctta gatagtgatg aaagacata tttgaattgg    120 ttatttcaga ggccaggcca gtctccaaag cgccttattt atctggtgtc tgaactggac    180
tctggagtcc ctgacaggtt cactggcagt ggatcaggga cagatttcac actgaaaatc    240
agcagagtgg aggctgagga tttgggagtt tattattgct ggcaaggtac acattttcct    300
cggacgttcg gtggaggcac caagctggaa atcaaacgg                            339

<210> SEQ ID NO 39
<211> LENGTH: 351
<212> TYPE: DNA
<213> ORGANISM: Artificial
<220> FEATURE:
<223> OTHER INFORMATION: HA heavy chain variable region

<400> SEQUENCE: 39
caggtgcagc tggtgcagtc tggagctgag gtgaagaagc ctggagcctc tgtgaaggtg     60
tcctgtaagg cctctggcta caccttcaca ggctacttca tgaactgggt gaggcaggcc    120
cctggccagg gctggagtg gatgggcctg atcaaccctt acaatggaga ctccttctac    180
aaccagaagt tcaagggcag ggtgaccatg accagggaca cctccacctc cacagtgtac    240
atggagctgt cctccctgag gtctgaggac acagctgtgt actactgtgc caggggcctg    300
aggagggact tgactactg gggccagggc accctggtga cagtgtcctc c               351

<210> SEQ ID NO 40
<211> LENGTH: 351
<212> TYPE: DNA
<213> ORGANISM: Artificial

<220> FEATURE:
<223> OTHER INFORMATION: HB heavy chain variable region

<400> SEQUENCE: 40

| caggtgcagc | tggtgcagtc | tggagctgag | gtgaagaagc | ctggagcctc | tgtgaaggtg | 60 |
| tcctgtaagg | cctctggcta | cagcttctct | ggctacttca | tgaactgggt | gaggcaggcc | 120 |
| cctggccagg | gcctggagtg | gatgggcctg | atcaacccctt | acaatggaga | ctccttctac | 180 |
| aaccagaagt | tcaagggcag | ggtgaccatg | accaggaca | cctccacctc | cacagtgtac | 240 |
| atggagctgt | cctccctgag | gtctgaggac | acagctgtgt | actactgtgc | caggggcctg | 300 |
| aggagggact | ttgactactg | gggccagggc | accctggtga | cagtgtcctc | c | 351 |

<210> SEQ ID NO 41
<211> LENGTH: 351
<212> TYPE: DNA
<213> ORGANISM: Artificial
<220> FEATURE:
<223> OTHER INFORMATION: HL heavy chain variable region

<400> SEQUENCE: 41

| caggtgcagc | tggtgcagtc | tggagctgag | gtgaagaagc | ctggagcctc | tgtgaaggtg | 60 |
| tcctgtaagg | cctctggcta | cagcttctct | ggctacttca | tgaactgggt | gaggcaggcc | 120 |
| cctggccagg | gcctggagtg | gatgggcctg | atcaacccctt | acaatggaga | ctccttctac | 180 |
| aaccagaagt | tcaagggcag | ggtgaccatg | accaggaca | agtcctcctc | cacagcttac | 240 |
| atggagctgt | cctccctgag | gtctgaggac | acagctgtgt | actactgtgc | caggggcctg | 300 |
| aggagggact | ttgactactg | gggccagggc | accctggtga | cagtgtcctc | c | 351 |

<210> SEQ ID NO 42
<211> LENGTH: 351
<212> TYPE: DNA
<213> ORGANISM: Artificial
<220> FEATURE:
<223> OTHER INFORMATION: HT heavy chain variable region

<400> SEQUENCE: 42

| caggtgcagc | tggtgcagtc | tggagctgag | gtgaagaagc | ctggagcctc | tgtgaaggtg | 60 |
| tcctgtaagg | cctctggcta | cagcttctct | ggctacttca | tgaactgggt | gaggcaggcc | 120 |
| cctggccagg | gcctggagtg | gatgggcctg | atcaacccctt | acaatggaga | ctccttctac | 180 |
| aaccagaagt | tcaagggcag | ggtgaccatg | accaggcaga | cctccacctc | cacagtgtac | 240 |
| atggagctgt | cctccctgag | gtctgaggac | acagctgtgt | actactgtgt | caggggcctg | 300 |
| aggagggact | ttgactactg | gggccagggc | accctggtga | cagtgtcctc | c | 351 |

<210> SEQ ID NO 43
<211> LENGTH: 351
<212> TYPE: DNA
<213> ORGANISM: Artificial
<220> FEATURE:
<223> OTHER INFORMATION: HN heavy chain variable region

<400> SEQUENCE: 43

| caggtgcagc | tggtgcagtc | tggagctgag | gtgaagaagc | ctggagcctc | tgtgaaggtg | 60 |
| tcctgtaagg | cctctggcta | cagcttctct | ggctacttca | tgaactgggt | gaggcaggcc | 120 |
| cctggccagg | gcctggagtg | gatgggcctg | atcaacccctt | acaatggaga | ctccttctac | 180 |
| aaccagaagt | tcaagggcag | ggtgaccatg | accaggcaga | cctccacctc | cacagtgtac | 240 |

```
atggagctgt cctccctgag gtctgaggac acagctgtgt actactgtgc caggggcctg    300
aggagggact ttgactactg gggccagggc accctggtga cagtgtcctc c            351
```

<210> SEQ ID NO 44
<211> LENGTH: 351
<212> TYPE: DNA
<213> ORGANISM: Artificial
<220> FEATURE:
<223> OTHER INFORMATION: HU heavy chain variable region

<400> SEQUENCE: 44

```
caggtgcagc tggtgcagtc tggagctgag gtgaagaagc ctggagcctc tgtgaaggtg    60
tcctgtaagg cctctggcta cagcttctct ggctacttca tgaactgggt gaggcaggcc    120
cctggccagg gcctggagtg gatgggcctg atcaacccct acaatggaga ctccttctac    180
aaccagaagt tcaagggcag ggtgaccatg accaggcaga gtcctcctc cacagcttac     240 atggagctgt cctccctgag gtctgaggac acagctgtgt actactgtgt caggggcctg    300
aggagggact ttgactactg gggccagggc accctggtga cagtgtcctc c            351
```

<210> SEQ ID NO 45
<211> LENGTH: 339
<212> TYPE: DNA
<213> ORGANISM: Artificial
<220> FEATURE:
<223> OTHER INFORMATION: LA light chain variable region

<400> SEQUENCE: 45

```
gatgtggtga tgacccagtc ccctctgtcc ctgcctgtga ccctgggcca gcctgcctcc    60
atctcctgta agtcctccca gtccctgctg gactctgatg gcaagaccta cctgaactgg    120
ttccagcaga ggcctggcca gtcccctagg aggctgatct acctggtgtc tgagctggac    180
tctggagtgc ctgacaggtt ctctggctct ggctctggca cagacttcac cctgaagatc    240
tccagggtgg aggctgagga tgtgggagtg tactactgtt ggcagggcac ccacttccct    300
aggacctttg gaggtggaac caagctggag atcaagcgt                          339
```

<210> SEQ ID NO 46
<211> LENGTH: 339
<212> TYPE: DNA
<213> ORGANISM: Artificial
<220> FEATURE:
<223> OTHER INFORMATION: LC light chain variable region

<400> SEQUENCE: 46

```
gatgtggtga tgacccagtc ccctctgtcc ctgcctgtga ccctgggcca gcctgcctcc    60
atctcctgta agtcctccca gtccctgctg gactctgatg gcaagaccta cctgaactgg    120
ctgttccaga ggcctggcca gtcccctagg aggctgatct acctggtgtc tgagctggac    180
tctggagtgc ctgacaggtt ctctggctct ggctctggca cagacttcac cctgaagatc    240
tccagggtgg aggctgagga tgtgggagtg tactactgtt ggcagggcac ccacttccct    300
aggacctttg gaggtggaac caagctggag atcaagcgt                          339
```

<210> SEQ ID NO 47
<211> LENGTH: 339
<212> TYPE: DNA
<213> ORGANISM: Artificial
<220> FEATURE:
<223> OTHER INFORMATION: LF light chain variable region

```
<400> SEQUENCE: 47
gatgtggtga tgacccagtc ccctctgtcc ctgcctgtga ccctgggcca gcctgcctcc      60
ctgttctgta agtcctccca gtccctgctg gactctgatg caagaccta cctgaactgg     120 ctgttccaga ggcctggcca gtcccctaag aggctgatct acctggtgtc tgagctggac    180
tctggagtgc ctgacaggtt cacaggctct ggctctggca cagacttcac cctgaagatc    240
tccagggtgg aggctgagga tgtgggagtg tactactgtt ggcagggcac ccacttccct    300
aggacctttg gaggtggaac caagctggag atcaagcgt                           339

<210> SEQ ID NO 48
<211> LENGTH: 339
<212> TYPE: DNA
<213> ORGANISM: Artificial
<220> FEATURE:
<223> OTHER INFORMATION: LG light chain variable region

<400> SEQUENCE: 48
gatgtggtgc tgacccagtc ccctctgtcc ctgcctgtga ccctgggcca gcctgcctcc     60
atctcctgta agtcctccca gtccctgctg gactctgatg caagaccta cctgaactgg    120 ctgttccaga ggcctggcca gtcccctagg aggctgatct acctggtgtc tgagctggac   180
tctggagtgc ctgacaggtt ctctggctct ggctctggca cagacttcac cctgaagatc   240
tccagggtgg aggctgagga tgtgggagtg tactactgtt ggcagggcac ccacttccct   300
aggacctttg gaggtggaac caagctggag atcaagcgt                          339

<210> SEQ ID NO 49
<211> LENGTH: 57
<212> TYPE: DNA
<213> ORGANISM: Artificial
<220> FEATURE:
<223> OTHER INFORMATION: murine heavy chain variable region signal
      peptide

<400> SEQUENCE: 49
atgggatgga gctgtatctt tctctttctc ctgtcagtaa ctgtaggtgt gttctct        57

<210> SEQ ID NO 50
<211> LENGTH: 57
<212> TYPE: DNA
<213> ORGANISM: Artificial
<220> FEATURE:
<223> OTHER INFORMATION: human heavy chain variable region signal
      peptide

<400> SEQUENCE: 50
atggcttggg tgtggacctt gctattcctg atggcagctg cccaaagtgc ccaagca        57

<210> SEQ ID NO 51
<211> LENGTH: 57
<212> TYPE: DNA
<213> ORGANISM: Artificial
<220> FEATURE:
<223> OTHER INFORMATION: murine light chain variable region signal
      peptide

<400> SEQUENCE: 51
atgagtcctg cccagttcct gtttctgtta gtgctctgga ttcgggaaac caacggt        57
```

```
<210> SEQ ID NO 52
<211> LENGTH: 57
<212> TYPE: DNA
<213> ORGANISM: Artificial
<220> FEATURE:
<223> OTHER INFORMATION: human light chain variable region signal
      peptide

<400> SEQUENCE: 52
atgaagttgc ctgttaggct gttggtgctg atgttctgga ttcctgcttc cagcagt      57

<210> SEQ ID NO 53
<211> LENGTH: 990
<212> TYPE: DNA
<213> ORGANISM: Artificial
<220> FEATURE:
<223> OTHER INFORMATION: human IgG1 heavy chain constant region

<400> SEQUENCE: 53
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggggg     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                      990

<210> SEQ ID NO 54
<211> LENGTH: 318
<212> TYPE: DNA
<213> ORGANISM: Artificial
<220> FEATURE:
<223> OTHER INFORMATION: human kappa light chain constant domain

<400> SEQUENCE: 54
actgtggcgg cgccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgt                                                   318
```

<210> SEQ ID NO 55
<211> LENGTH: 990
<212> TYPE: DNA
<213> ORGANISM: Artificial
<220> FEATURE:
<223> OTHER INFORMATION: human IgG1 heavy chain constant region S239C mutant

<400> SEQUENCE: 55

```
gctagcacca agggcccatc tgtcttcccc ctggcaccct cctccaagag cacctctggg      60
ggcacagctg ccctgggctg cctggtcaag gactacttcc ctgaacctgt gacagtgtcc     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctgggggga     360
ccgtgtgtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacaca     960
cagaagagcc tctccctgtc tccgggtaaa                                      990
```